(12) United States Patent
Brown

(10) Patent No.: US 8,642,610 B2
(45) Date of Patent: Feb. 4, 2014

(54) DUAL SMALL MOLECULE INHIBITORS OF CANCER AND ANGIOGENESIS

(75) Inventor: Milton L. Brown, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/366,726

(22) Filed: Feb. 6, 2012

(65) Prior Publication Data

US 2012/0202800 A1    Aug. 9, 2012

Related U.S. Application Data

(62) Division of application No. 11/628,209, filed as application No. PCT/US2005/019244 on Jun. 1, 2005, now Pat. No. 8,178,545.

(60) Provisional application No. 60/575,927, filed on Jun. 1, 2004.

(51) Int. Cl.
*A01N 43/54* (2006.01)
*A61K 31/517* (2006.01)
*C07D 239/72* (2006.01)

(52) U.S. Cl.
USPC ............ 514/266.31; 514/212.07; 544/289; 544/460; 544/523; 546/70; 546/141

(58) Field of Classification Search
USPC ........ 514/266.31, 212.07; 544/289, 460, 523; 546/70, 141
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Teeuwes | |
| 4,265,874 A | 5/1981 | Bonsen et al. | |
| 4,587,538 A | 5/1986 | Shanton et al. | |
| 5,401,752 A | 3/1995 | Tokunaga et al. | |
| 5,480,833 A | 1/1996 | Kikkawa et al. | |
| 5,480,883 A | 1/1996 | Spada et al. | |
| 6,187,923 B1 | 2/2001 | Dener et al. | |
| 6,716,614 B1 | 4/2004 | Donoho et al. | |
| 8,298,512 B2 | 10/2012 | Brown | |
| 2002/0137068 A1 | 9/2002 | Haugland et al. | |
| 2004/0122030 A1 | 6/2004 | Brown | |
| 2005/0130897 A1 | 6/2005 | Ma | |
| 2005/0214807 A1 | 9/2005 | Johnson et al. | |
| 2006/0148830 A1 | 7/2006 | Terakado et al. | |
| 2007/0134161 A1 | 6/2007 | Brown et al. | |
| 2007/0244098 A1 | 10/2007 | Brown | |

FOREIGN PATENT DOCUMENTS

| | | |
|---|---|---|
| AU | 2005249527 B2 | 11/2011 |
| EP | 0145225 A2 | 6/1985 |
| EP | 0145225 B1 | 10/1989 |
| EP | 0495610 A1 | 7/1992 |
| EP | 0495610 B1 | 6/1997 |
| JP | 62258368 A | 11/1987 |
| WO | WO-9823620 A1 | 6/1998 |
| WO | WO-9911623 A1 | 3/1999 |
| WO | WO-0027831 A1 | 5/2000 |
| WO | WO-0228841 A2 | 4/2002 |
| WO | WO-02086078 A3 | 10/2002 |
| WO | WO-2004031118 A1 | 4/2004 |
| WO | WO-2005117876 A1 | 12/2005 |

OTHER PUBLICATIONS

Pinedo et al., The Oncologist (2000) 2000-5(suppl 1) 1-2.*
McMahon et al., The Oncologist (2000) 2000-5(suppl 1 )3-10.*
"Australian Application Serial No. 2011244923, Office Action mailed Sep. 11, 2012", 4 pgs.
"Korean Application Serial No. 10-2006-7027847, Response filed Sep. 3, 2012 to Office Action mailed Mar. 2, 2012", With English Claims, 112 pgs.
"Canadian Application Serial No. 2,568,622, Office Action mailed Feb. 5, 2013", 2 pgs.
"Canadian Application Serial No. 2568622, Response filed Jan. 10, 2013 to Office Action mailed Jul. 10, 2012", 26 pgs.
"European Application Serial No. 05756099.7, Examination Notification Art. 94(3) mailed Feb. 5, 2013", 4 pgs.
"U.S. Appl. No. 11/613,663, Final Office Action mailed Sep. 12, 2011", 20 pgs.
"U.S. Appl. No. 11/613,663, Non Final Office Action mailed Dec. 13, 2011", 16 pgs.
"U.S. Appl. No. 11/613,663, Non Final Office Action mailed Apr. 13, 2011", 15 pgs.
"U.S. Appl. No. 11/613,663, Non Final Office Action mailed Sep. 28, 2010", 13 pgs.
"U.S. Appl. No. 11/613,663, Response filed Jan. 28, 2011 to Non Final Office Action mailed Sep. 28, 2010", 15 pgs.
"U.S. Appl. No. 11/613,663, Response filed Nov. 9, 2011 to Final Office Action mail Sep. 12, 2011", 15 pgs.
"U.S. Appl. No. 11/613,663, Response filed Jul. 12, 2011 to Non Final Office Action mailed Apr. 13, 2011", 15 pgs.
"U.S. Appl. No. 11/628,209, Non Final Office Action mailed Sep. 20, 2011", 18 pgs.
"U.S. Appl. No. 11/628,209, Notice of Allowability mailed Jan. 26, 2012", 3 pgs.
"U.S. Appl. No. 11/628,209, Notice of Allowance mailed Dec. 27, 2011", 7pgs.
"U.S. Appl. No. 11/628,209, Preliminary Amendment mailed Dec. 1, 2006", 3 pgs.

(Continued)

*Primary Examiner* — Paul V. Ward
(74) *Attorney, Agent, or Firm* — Schwegman, Lundberg & Woessner, P.A.

(57) ABSTRACT

The present invention provides analogs and derivatives of thalidomide which inhibit cancer and angiogenesis. The present invention further provides compounds which disrupt microtubule polymerization. The present further provides methods of treating cancers comprising mutant p53.

19 Claims, 5 Drawing Sheets

(56) References Cited

OTHER PUBLICATIONS

"U.S. Appl. No. 11/628,209, Response filed Feb. 6, 2012 to Notice of Allowance mailed Dec. 27, 2011", 3 pgs.
"U.S. Appl. No. 11/628,209, Response filed Jul. 29, 2011 to Restriction Requirement mailed Jul. 1, 2011", 21 pgs.
"U.S. Appl. No. 11/628,209, Response filed Oct. 31, 2011 to Non Final Office Action mailed Sep. 20, 2011", 13 pgs.
"U.S. Appl. No. 11/628,209, Restriction Requirement mailed Jul. 1, 2011", 10 pgs.
"Australian Application Serial No. 2005249527, First Examination Report mailed Dec. 9, 2009", 2 pgs.
"Australian Application Serial No. 2005249527, Response filed Jun. 29, 2011 to Examiner Report mailed Dec. 9, 2009", 29 pgs.
"European Application Serial No. 05756099.7, European Search Report mailed Nov. 15, 2007", 3 pgs.
"European Application Serial No. 05756099.7, Examination Report mailed Oct. 11, 2011", 7 pgs.
"European Application Serial No. 05756099.7, Office Action Response filed Jan. 27, 2012", 26 pgs.
"International Application Serial No. PCT/US2005/019244, International Preliminary Examination Report mailed Dec. 4, 2006", 6 pgs.
"International Application Serial No. PCT/US2005/019244, International Search Report and Written Opinion mailed Oct. 14, 2005", 10 pgs.
"Israeli Application Serial No. 11/613,663, Office Action Response Filed Apr. 3, 2011", 2 pgs.
"Israeli Application Serial No. 179714, Non Final Office Action mailed Aug. 3, 2010", 2.
"Israeli Application Serial No. 179714, Office Action mailed Dec. 24, 2011", 2 pgs.
"Japanese Application Serial No. 2007-515530, Office Action mailed Jun. 7, 2011", 10 pgs.
"Japanese Application Serial No. 2007-515530, Office Action Response filed Oct. 5, 2011", 13 pgs.
"Keratitis", From Wikipedia, the free encyclopedia, (This page was last modified on Jan. 11, 2011).
"Singapore Application Serial No. 200608386-9, Search Report mailed Jan. 19, 2009", 9 pgs.
Altschul, S. F., "Basic Local Alignment Search Tool", J. Mol. Biol., 215(3), (1990), 403-410.
Altschul, S. F., "Gapped BLAST and PSI-BLAST: A New Generation of Protein Database Search Programs", Nucleic Acids Research, 25(17), (1997), 3389-3402.
Banerjee, A., et al., "A monoclonal antibody against the type II isotype of beta-tubulin. Preparation of isotypically altered tubulin.", J Biol Chem., 263(6), (Feb. 25, 1988), 3029-34.
Brem, H., et al., "Interstitial chemotherapy with drug polymer implants for the treatment of recurrent gliomas.", J Neurosurg., 74(3), (Mar. 1991), 441-6.
Brown, M. L, et al., "Comparative molecular field analysis of colchicine inhibition and tubulin polymerization for combretastatins binding to the colchicine binding site on beta-tubulin.", Bioorg Med Chem., 8(6), (Jun. 2000), 1433-41.
Carey, F. A, et al., "Carbonium ion-silane hydride transfer reactions. II. 2-Phenyl-2-norbornyl cation", J. Org. Chem., 34(1), (1969), 887-892.
Carles, G., et al., "Differentiation of human colon cancer cells changes the expression of beta-tubulin isotypes and MAPs.", Br J Cancer., 80(8), (Jun. 1999), 1162-8.
Cheon, S. H, et al., "Structure-activity relationship studies of isoquinolinone type anticancer agent", Arch Pharm Res., 24(4), (Aug. 2001), 276-80.
Cho, W. J, et al., "Molecular modeling of 3-arylisoquinoline antitumor agents active against A-549. A comparative molecular field analysis study", Bioorg Med Chem.,10(9), (Sep. 2002), 2953-61.
Griffin, R. J, et al., "Resistance-modifying agents. 5. Synthesis and biological properties of quinazolinone inhibitors of the DNA repair enzyme poly(ADP-ribose) polymerase (PARP).", J Med Chem., 41(26), (Dec. 17, 1998), 5247-56.
Hamel, E., et al., "Antitumor 2,3-dihydro-2-(aryl)-4(1H)-quinazolinone derivatives. Interactions with tubulin.", Biochem Pharmacol., 51(1), (Jan. 12, 1996), 53-59.
Hamel, Ernest, et al., "Antitumor 2, 3-Dihydro-2-(Aryl)-4(1H)-Quinazolinone Derivatives Interactions With Tublin", Biochemical Pharmacology Pergamon, Oxford, GB, vol. 51, No. 1, (Jan. 1, 1996), 53-59.
Hollstein, M., et al., "p53 mutations in human cancers.", Science, 253(5015), (Jul. 5, 1991), 49-53.
Holwell, S. E, et al., "Anti-tumor and anti-vascular effects of the novel tubulin-binding agent combretastatin A-1 phosphate.", Anticancer Res., 22(6C), (Nov.-Dec. 2002), 3933-40.
Hour, M. J, et al., "6-Alkylamino- and 2,3-dihydro-3'-methoxy-2-phenyl-4-quinazolinones and related compounds: their synthesis, cytotoxicity, and inhibition of tubulin polymerization.", J Med Chem., 43(23), (Nov. 16, 2000), 4479-87.
Jordan, M. A, "Mechanism of action of antitumor drugs that interact with microtubules and tubulin.", Curr Med Chem Anticancer Agents, 2(1), (Jan. 2002), 1-17.
Kamb, Alexander, "Wnat's wrong with our cancer models", Nature Reviews Drug Discovery, 2, (2005), 161-165.
Karlin, S., et al., "Applications and statistics for multiple high-scoring segments in molecular sequences.", Proc Natl Acad Sci U S A., 90(12), (Jun. 15, 1993), 5873-7.
Karlin, S., et al., "Methods for assessing the statistical significance of molecular sequence features by using general scoring schemes.", Proc Natl Acad Sci U S A., 87(6), (Mar. 1990), 2264-8.
Miller, K. D, et al., "Redefining the target: chemotherapeutics as antiangiogenics", J Clin Oncol., 19(4), (Feb. 15, 2001), 1195-206.
Moore, James A, et al., "Reactions of anthranilamide and o-aminoacetophenone with benzil and benzoin", J. Org. Chem., 34(4), (1969), 887-892.
Poupaert, Jacques H, "Drug Design: Basic Principles and Applications", In 2 Encyclopedia of Pharmaceutical Technology, (James Swarbrick ed., 3rd ed., ), (2007), 9 pgs.
Roach, M. C, et al., "Preparation of a monoclonal antibody specific for the class I isotype of beta-tubulin: the beta isotypes of tubulin differ in their cellular distributions within human tissues.", Cell Motil Cytoskeleton, 39(4), (1998), 273-85.
Rowinsky, E. K, et al., "Antimicrotule Agents", Cancer Principles and Practice of Oncology, 6th ed., vol. 1, (2001), 431-447.
Saclarides, T. J, et al., "Tumor angiogenesis and rectal carcinoma", Dis Colon Rectum., 37(9), (Sep. 1994), 921-6.
Safran, H., et al., "p53 mutations do not predict response to paclitaxel/radiation for nonsmall cell lung carcinoma.", Cancer, 78(6), (Sep. 15, 1996), 1203-10.
Sharpless, Norman E, et al., "The mighty mouse: genetically engineered mouse models in cancer drug development", Nature Reviews Drug Discovery 5, (2006), 14 pgs.
Silence, K., et al., "Fluorescence stopped-flow study of the interaction of tubulin with the antimitotic drug MDL 27048.", Biochemistry, 31(45), (Nov. 17, 1992), 11133-7.
Smith, Nicola F, et al., "The application of cassette dosing for pharmacokinetic screening in small-molecule cancer drug discovery", Molecular Cancer Therapeutics, 6,, (2007), 428-440.
Tinley, T. L, et al., "Novel 2-methoxyestradiol analogues with antitumor activity.", Cancer Res., 63(7), (Apr. 1, 2003), 1538-49.
Veljkovic, V., et al., "Application Of The EIIP/ISM Bioinformatics Concept in Development of New Drugs", Current Medicinal Chemistry, 14,, (2007), 441-453.
Verdier-Pinard, P., et al., "Analysis of tubulin isotypes and mutations from taxol-resistant cells by combined isoelectrofocusing and mass spectrometry", Biochemistry, 42(18), (May 13, 2003), 5349-57.
Xu, Keliang, et al., "Interaction of nocodazole with tubulin isotypes", Drug Development Research, 55(2), (Feb. 2002), 91-96.
Zon, Leonard I, et al., "In Vivo Drug Discovery in the Zebrafish", Nature Reviews Drug Discovery, 4, (Jan. 2005), 35-44.

* cited by examiner

Control

33 µM SC-2-71

Control 1.65 µM SC-2-71

DUAL SMALL MOLECULE INHIBITORS OF CANCER AND ANGIOGENESIS

CROSS REFERENCE TO RELATED APPLICATIONS

This application is a divisional of and claims the benefit of priority under 35 U.S.C. §120 to U.S. patent application Ser. No. 11/628,209, filed on Dec. 1, 2006, which is national stage filing under 35 U.S.C. §371 of International Application No. PCT/US2005/019244 filed on Jun. 1, 2005, which is entitled to priority pursuant to 35 U.S.C. §119(e) to U.S. provisional patent application No. 60/575,927, filed on Jun. 1, 2004, the benefit of priority of each of which is claimed hereby, and each of which are incorporated by reference herein in its entirety.

BACKGROUND

Colorectal cancer is the second most common cause of cancer-related mortality in Europe and North America. This cancer affects nearly 150,000 patients and results in more than 60,000 deaths in the United States per year. Despite significant advances in the management of the colon cancer patient, there has been little change in survival rates over the past 50 years. The primary cause of death relates to the development of distant metastases to organs such as the liver and lungs. Unfortunately, colon cancer still remains one of the most common types of epithelial malignancies in both genders and is essentially incurable when it reaches the most advanced stages.

Surgical resection remains the present standard of care for patients with localized colorectal cancer. Several adjuvant chemotherapy strategies have also emerged and the use of 5-fluorouracil (5-FU) with leucovorin (LV) rescue is now established in stage III colon cancer. Considering the high re-occurrence rates of colon cancer and the side-effects of surgical and chemical therapies, the discover of novel compounds that block, reverse, delay or prevent the development of invasive large bowel neoplasms would be of major importance.

Adenocarcinoma accounts for 90-95% of all colorectal cancer and the majority of the human cultured cell lines reflect this phenotype. Table 1 summarizes the differences in some available human colon cell lines in relation to age, gender, histology/grade, and source (i.e., ascites vs. primary tumor). These cultured cell lines provide a rich opportunity to evaluate novel compounds for efficacy and to establish their mechanism of action.

TABLE 1

NCI cultured human colon cancer cell lines.

| Cell line[a] | Gender | Patient Age | Histology | Treatment | Source |
|---|---|---|---|---|---|
| COLO 205 | M | 70 | Adenocarcinoma | Y | Ascites |
| HCC-2998 | | | Carcinoma | N | |
| HCT-15 | | | Adenocarcinoma | | |
| HCT-116 | | | Adenocarcinoma/grade III | | |
| HT29 | F | 44 | Adenocarcinoma | | Primary |
| KM12 | | | Adenocarcinoma | | |
| SW-60 | M | 51 | Adenocarcinoma | N | Metastasis |

[a]Available cell lines from the National Cancer Institute (NCI).

Tubulin, the subunit protein of cellular microtubules, is the target of several effective cancer chemotherapeutic agents currently in clinical use. Tubulin is composed of an α/β Heterodimer, and at least six human α-tubulin and seven human β-tubulin isotypes (gene products) are known. Overall, the repertoire of β-tubulin isotypes is believed to play a significant role in development and the building of specialized microtubule-based cellular structures, and general disruption of cellular microtubules is one target for cancer chemotherapy that has proven to be effective.

In many organisms, both α and β tubulin isotypes differ by their tissue distributions. In mammals, the $\beta_I$ and $\beta_{IV}$ isotypes are quite widespread, and $\beta_{II}$ is less so, while $\beta_{III}$ and $\beta_{VI}$ have narrow distributions and $\beta_V$ distribution is unknown. As a tool for localizing the isotypes, the preparation of monoclonal antibodies specific for $\beta_I$, $\beta_{III}$, $\beta_{IV}$ and $\beta_V$ isotypes have been reported (Banerjee et al., J. Biol. Chem. 1988, 263:3029-3034). β-isotypes have been localized in several human tissues including oviduct, skin, colon, and pancreas with striking differences in their tissue distributions. In fact, there is little or no $\beta_{III}$ in these tissues, except for the columnar epithelial cells of the colon (Roach et al., Cell Motility and the Cytoskeleton 1998, 39:4:273-285).

Normal cellular architecture, growth, division, and intracellular transport are dependent on microtubules. Microtubules are versatile and highly dynamic structures that undergo rapid changes in response to cellular signaling from a variety of stimuli. The dynamic instability of microtubules is critical for their normal functions. Drugs that disrupt the dynamic response of microtubules can lead to altered microtubule function, abnormal cellular metabolism, and can ultimately lead to apoptosis.

In cell lines resistant to microtubule-stabilizing drugs that express heterozygous tubulin mutations, the relative amount of mutant tubulin expression is important. In these cell lines, the absence of beta II- and beta IVa-tubulin has been demonstrated, and an increased level of expression of beta IIII-tubulin in resistant cells has been confirmed (Verdier-Pinard et al., Biochemistry, 42(18):5349-57, 2003), indicating that this tubulin isotype may have a significant role in taxol resistance. Accordingly, the present invention is directed to selective tubulin inhibitors and the use of such inhibitors to selectively regulate the expression and localization of f3-tubulin isotypes in tissues as a means of treating cancers that previously were difficult to treat using chemotherapeutics.

Antimicrotubule agents comprise some of the most widely used and effective cancer chemotherapeutic agents in clinical use (Rowinsky, E. K. and Tolcher, A. W. Antimicrotubule Agents. In: V. T. J. DeVita, S. Hellman, and S. A. Rosenberg (eds.), Cancer Principles and Practice of Oncology, 6th edition, Vol. 1, pp. 431-447. Philadelphia, Pa.: Lippincott, Williams and Wilkins, 2001). Prompted by the clinical successes of the vinca alkaloids and taxanes, significant efforts have been focused on identifying new agents that have a similar mechanism of action, but superior properties including the ability to circumvent drug resistance mechanisms, exhibit better solubility and oral availability.

A serious problem associated with the treatment of cancer is the development of drug resistance. Some tumors are intrinsically resistant to chemotherapy and others develop drug resistance during chemotherapy. A significant proportion of tumors are multidrug resistant because of overexpression of membrane proteins that act as drug efflux pumps. Overexpression of the MDR-1 gene product, P-glycoprotein (Pgp), leads to diminished intracellular drug accumulation and to attenuated cytotoxic effects. Clinically, multidrug resistance imparted by the expression of Pgp can limit the utility of many currently available agents including vinblastine, vincristine, taxol and docetaxol. There is a clear need for new drugs that can circumvent multidrug resistance.

A second major reason for the development of new microtubule-active agents is that microtubule disruptors are in some cases effective against tumors that express abnormal p53. The tumor suppressor gene encoding p53 is the most frequently mutated gene in human cancers. It is estimated that half of all cancers in the United States exhibit altered p53 (Hollstein et al. Science, 253: 49-53, 1991).

In addition, compounds that target cellular microtubules have recently been found to exhibit antiangiogenic activities and this may contribute to their antitumor and anticancer efficacies (Miller, et al., J. Clin. Oncol. 19, 1195-1206, 2001). The taxanes, taxol and docetaxel, vinblastine, vincristine, combretastatin (Holwell et al., Anticancer Research. 22(6C): 3933-40, 2002) and 2-methoxyestradiol all have antiangiogenic activity in vivo (Miller, et al., J. Clin. Oncol., 19:1195-1206, 2001). Angiogenesis is the process by which new blood vessels are formed from pre-existing blood vessels. This process is complex and begins with the degradation of the basement membrane by proteases secreted by activated endothelial cells. Migration and proliferation leads to the formation of solid endothelial cell sprouts into the stromal space. Vascular loops and capillary tubes develop with formation of tight junctions and deposition of new basement membrane. This process is important in normal reproduction, embryonic development, and wound healing. However, improperly regulated angiogenesis has been implicated in many diseases including cancer.

Tumor growth requires the formation of new blood vessels, (i.e., angiogenesis). It is believed that tumor cells initiate and maintain angiogenesis by expressing a network of angiogenic factors, including endothelial growth factors such as vascular endothelial growth factor (VEGF), angiogenic cytokines such as interleukin-8 (IL-8), matrix metalloproteinases (MMP) such as MMP-2 and MMP-9, and adhesion molecules such as integrins and cadherins. Considering the relevance of angiogenesis in tumor progression, anti-angiogenic therapies have emerged as a potentially promising modality of cancer therapy. A variety of purely anti-angiogenic strategies have been developed, including: 1) endogenous angiogenesis inhibitors (e.g., endostatin); 2) blockers of endothelial survival and growth factors/receptors (e.g., VEGF antibody and VEGF receptor tyrosine kinase inhibitor SU6668); and 3) inhibitors of adhesion molecules or MMPs (e.g., antibodies against integrin). Unfortunately, the use of anti-angiogenic agents to treat cancer has proved challenging and purely anti-angiogenic strategies have failed in the clinic. While these agents inhibit tumor angiogenesis in animal studies, complete suppression of angiogenesis or tumor shrinkage in patients has been uncommon.

There is a long felt need in the art for a better method to identify and prepare compounds capable of regulating cancer cells, angiogenesis, endothelial cells, and tumor formation. The present invention satisfies these needs.

SUMMARY OF THE INVENTION

The present invention is directed to a series of compounds that have anti-microtubulin and/or anti-angiogenic activity. Such compounds, and compositions comprising these compounds, can be used to treat neoplastic diseases and other proliferative disorders, diseases, and conditions associated with excessive or uncontrolled growth of cells, such as tumors. The invention encompasses inhibiting or impeding supplying blood to tissues or cells such as cancer, including inhibiting vascular endothelial cells. These compounds have the general structure of formula I:

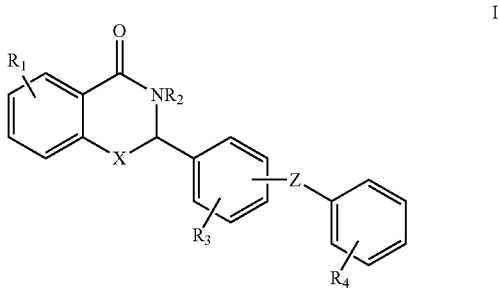

wherein $R_1$, $R_3$ and $R_4$ are independently selected from the group consisting of H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl or $R_3$ and $R_2$ taken together with the atoms to which they are attached form an optionally substituted heterocyclic fused ring, or $R_3$ and $R_4$ taken together with the atoms to which they are attached form an optionally substituted cycloalkyl fused ring;

X is selected from the group consisting of $NR_5$, —(NH $(CH_2)_n$)—, $CH_2$, $CHR_5$ and CO; wherein n is 1 or 2;

Z is selected from the group consisting of a bond, O, NH, S, CO, COO, $CH_2O$, $CH_2NH$, CONH, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl, or $R_3$ and $R_5$ taken together with the atoms to which they are attached form an optionally substituted heterocyclic fused ring.

DETAILED DESCRIPTION OF THE INVENTION

Figure 1:
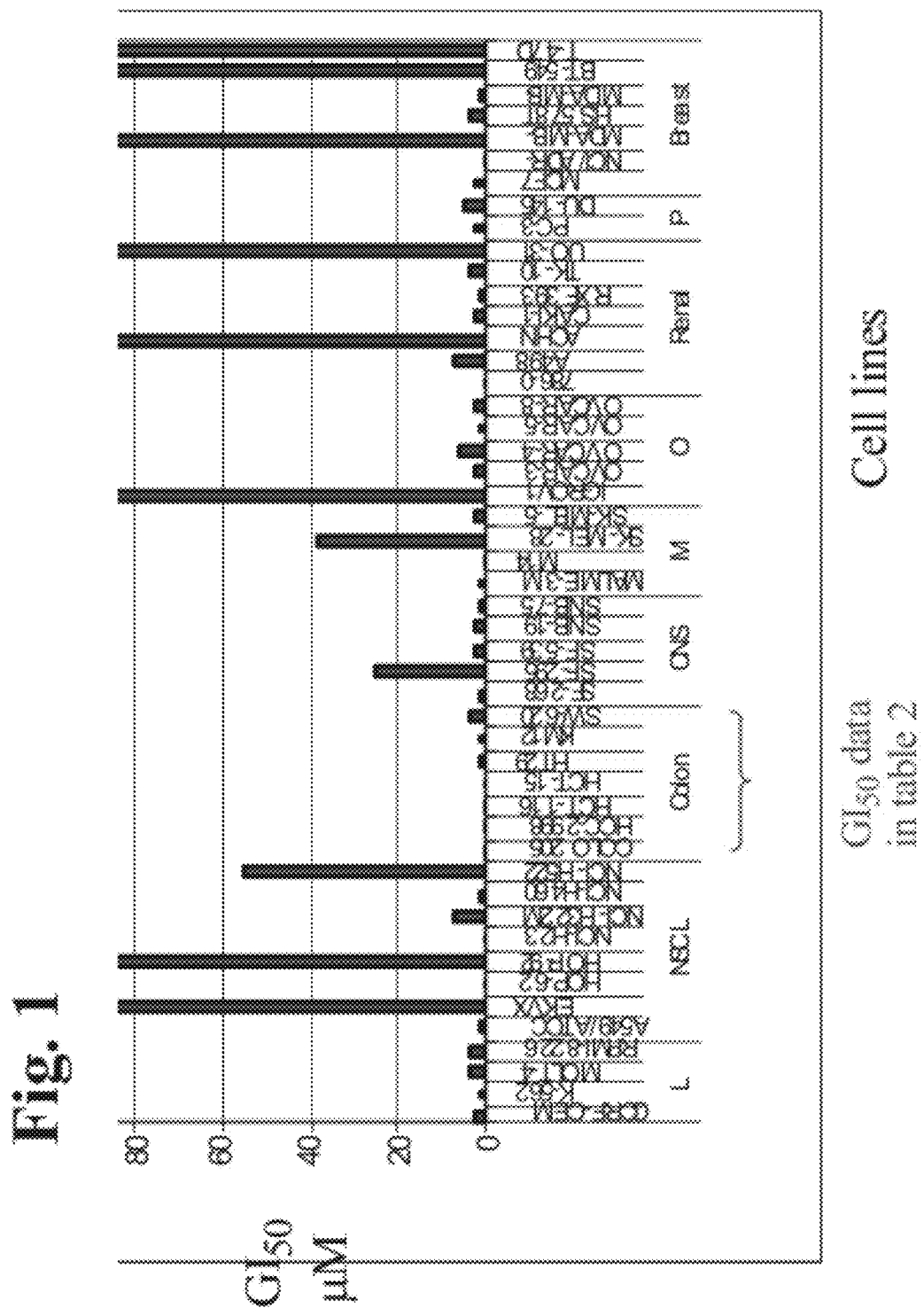
FIG. 1 Depicts the effects of SC-2-71 against the NI 60 human cell lines ($GI_{50}$).

Abbreviations
5FU—5-fluorouracil
CAM—chick chorioallantoic membrane
CoMFA—comparative molecular field analysis
HMEC—human microvessel endothelial cell
HUVEC—human umbilical vein endothelial cell
IL—interleukin
LV—leucovorin
MDR—multidrug resistant
MMP—matrix metalloproteinases MVD—microvessel density
Pgp—P glycoprotein
Rr—relative resistance
VEGF—vascular endothelial growth factor
Definitions In describing and claiming the invention, the following terminology will be used in accordance with the definitions set forth below.

As used herein, the articles "a" and "an" refer to one or to more than one, i.e., to at least one, of the grammatical object of the article. By way of example, "an element" means one element or more than one element.

A disease or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

"Angiogenesis-associated" disease or disorder refers to a disease or disorder associated with aberrant angiogenesis or a disease or disorder reliant on angiogenesis. Changes in microvessel density are encompassed within the term "angiogenesis-associated."

"Anti-proliferative," as used herein, refers to the ability of a compound to impede or inhibit cell proliferation. As such, the compound may act directly on a cell or may act indirectly. For example, in the context of cancer, a cancer cell can be inhibited from proliferating by depriving it of blood supply. The term "anti-proliferative" does not refer to a particular mechanism by which proliferation is inhibited or impeded.

The term "cancer," as used herein, is defined as proliferation of cells whose unique trait—loss of normal controls—results new characteristics such as unregulated growth, lack of differentiation, local tissue invasion, and metastasis. Examples include, but are not limited to, breast cancer, prostate cancer, ovarian cancer, cervical cancer, skin cancer, melanoma, pancreatic cancer, colorectal cancer, renal cancer, leukemia, non small cell carcinoma, and lung cancer.

As used herein, a "derivative" of a compound refers to a chemical compound that may be produced from another compound of similar structure in one or more steps, as in replacement of H by an alkyl, acyl, or amino group.

The term "disrupt" as used herein refers to the ability of a compound of the invention to inhibit microtubules from polymerizing or the ability of a compound of the invention to induce at least partial depolymerization of microtubules.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound of the invention to reduce or impede a described function, such as cell proliferation, tumor growth, or angiogenesis. Preferably, inhibition is by at least 10%, more preferably by at least 25%, even more preferably by at least 50%, and most preferably, the function is inhibited by at least 75%.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "subject" of diagnosis or treatment is a mammal, including a human. As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, an "effective amount" means an amount sufficient to produce a selected effect. For example, an effective amount of an antimicrotubule agent is an amount that disrupts the dynamic response of microtubulins.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear allyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. AOptionally substituted aryl@ includes aryl compounds having from zero to four substituents, and Asubstituted aryl@ includes aryl compounds having one or more substituents. The term ($C_5$-$C_8$ alkyl)aryl refers to any aryl group which is attached to the parent moiety via the alkyl group.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

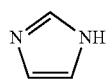

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Embodiments of the Invention

Thalidomide (shown below) was developed in the 1950s by Chemie Grünenthal of Germany as a non-toxic sedative. It was widely used to prevent morning sickness in pregnant women.

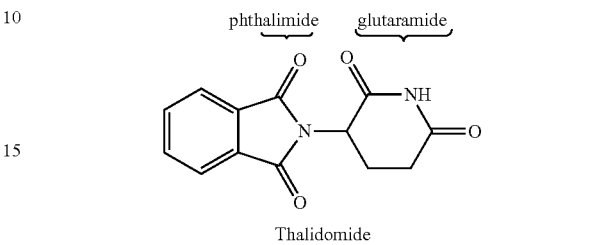

Thalidomide

In addition to its sedative effects in humans, an association was reported of teratogenic limb defects from maternal thalidomide usage. Aside from this serious teratogenic effect on the fetus, the drug does have therapeutic value: (1) for its immunosuppressive effect in the treatment of graft versus host disease; (2) in the treatment of leprosy; and (3) for inflammatory dermatoses. Furthermore, thalidomide has significant anti-angiogenic activity, and as a result, is finding more extensive clinical use in the treatment of various cancers, particularly in cancers having a poor prognosis due to microvessel density (e.g. multiple myeloma and prostate). Anti-angiogenic thalidomide derivatives have been previously described, including a derivative wherein the glutaramide ring is replaced with a phenyl group, leading to an active compound named, BROWN1.

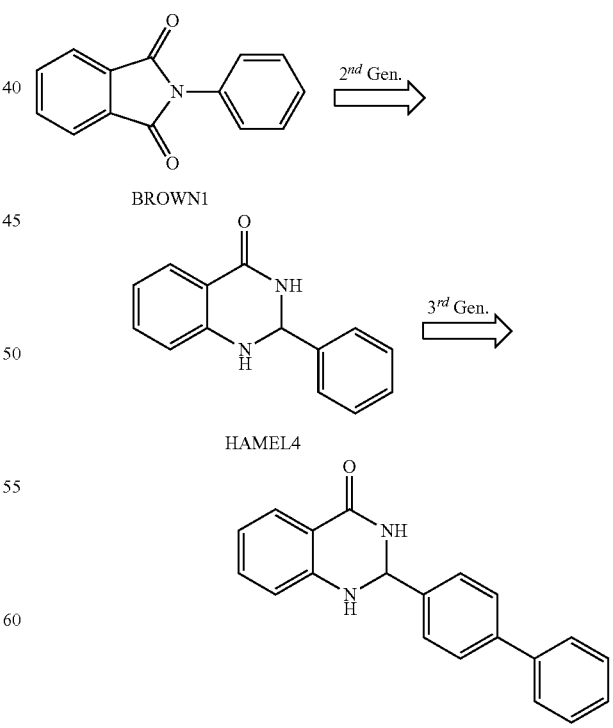

Second generation analogues were conceived by a ring expansion of the phthalimide ring, which resulted in the previously reported quinazolinone (HAMEL4; see published PCT application no. WO 02/086078A3, the disclosure of which is incorporated in its entirety herein). HAMEL4 has now been further optimized herein to generate novel compound SC-2-71, which as disclosed herein has enhanced efficacy (relative to HAMEL4) against various cancers, including solid tumors such as colon cancer.

In accordance with the present invention, a compound is provided having the general structure:

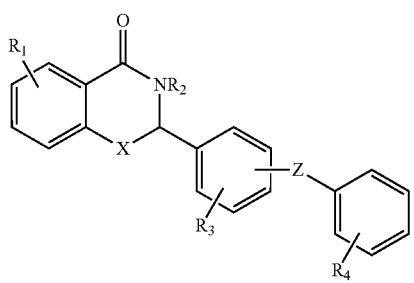

I wherein $R_1$ is independently selected from the group consisting of $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri-chloro and mono-, bi, and tri-methyl ($CH_3$);

wherein $R_3$ and $R_4$ are independently selected from the group consisting of $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri-chloro and mono-, bi, and tri-methyl ($CH_3$), or $R_3$ and $R_2$ taken together with the atoms to which they are attached form an optionally substituted heterocyclic fused ring, or $R_3$ and $R_a$ taken together with the atoms to which they are attached form an optionally substituted cycloalkyl fused ring;

X is selected from the group consisting of $NR_5$, —(NH$(CH_2)_n$)—, $CH_2$, $CHR_5$ and CO; wherein n is 1 or 2;

Z is selected from the group consisting of a bond, O, NH, S, CO, COO, $CH_2$O, $CH_2$NH, CONH, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl, or $R_3$ and $R_5$ taken together with the atoms to which they are attached form an optionally substituted heterocyclic fused ring.

One of ordinary skill in the art would appreciate that compounds of the invention further encompass analogs, derivatives, and modification of Formula I.

In accordance with one embodiment the compound of Formula I is provided wherein $R_1$, $R_3$ and $R_4$ are independently selected from the group consisting of H, halo, $C_1$-$C_4$ alkyl, $C_2$-$C_4$ alkenyl, $C_2$-$C_4$ alkynyl and $C_5$-$C_6$ aryl;

X is selected from the group consisting of $NR_S$, —(NH$(CH_2)_n$)—, $CH_2$ and CO;

n is 1 or 2;

Z is selected from the group consisting of a bond, O, NH, S, CO, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In a further embodiment a compound of Formula I is provided wherein $R_1$, $R_3$ and $R_4$ are independently selected from the group consisting of H, halo and $C_1$-$C_4$ alkyl;

X is selected from the group consisting of $NR_S$, and CO;

Z is selected from the group consisting of a bond, CO and $C_1$-$C_4$ alkyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl. Furthermore it is anticipated that the hydrogen groups on the claimed compounds can be substituted with flourine atoms without significantly altering the activity of the parent compound.

In one aspect, $R_1$, $R_3$, and $R_4$ are each independently selected from the group consisting of mono-, bi-, and tri-chloro and mono-, bi, and tri-methyl ($CH_3$).

In one embodiment, the compound is

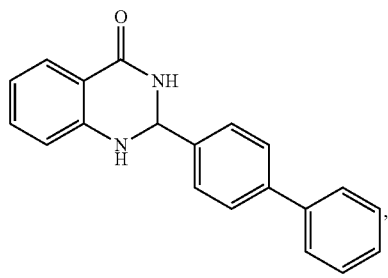

SC-2-71 or an analog, derivative, or modification thereof.

In one aspect, the analog, derivative, or modification of SC-2-71 is:

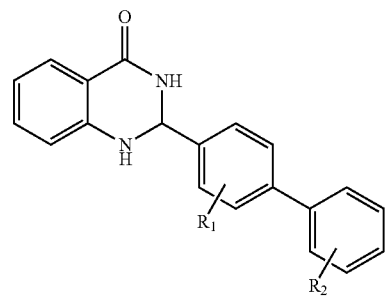

Aryl Substitution (Biphenyl)

| R1 | R2 |
|---|---|
| 2-Cl | H |
| 3-Cl | H |
| 2-$CH_3$ | H |
| 3-$CH_3$ | H |
| H | 2,3,4-Cl |
| H | 2,3,4-$CH_3$ |

In another aspect, $R_1$ and $R_2$ are independently mono-, di, or tri-chloro and mono-, di-, and tri-methyl ($CH_3$).

In accordance with one embodiment, the compound has the general structure:

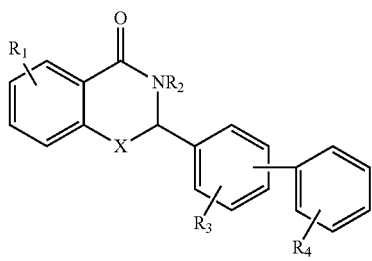

wherein $R_1$, $R_3$ and $R_4$ are independently selected from the group consisting of H, halo and $C_1$-$C_4$ alkyl;

X is selected from the group consisting of $NR_5$, —(NH$(CH_2)_n$)—, $CH_2$ and CO;

n is 1 or 2; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In one aspect, $R_1$, $R_3$, and $R_4$ are each independently selected from the group consisting of mono-, bi-, and tri-chloro and mono-, bi, and tri-methyl ($CH_3$).

In another embodiment of the compound has the general structure:

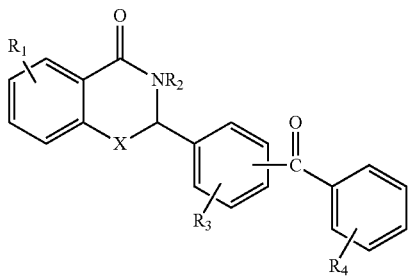

wherein $R_1$, $R_3$ and $R_4$ are independently selected from the group consisting of H, halo and $C_1$-$C_4$ alkyl;

X is selected from the group consisting of $NR_5$, —(NH$(CH_2)_n$)—, $CH_2$ and CO;

n is 1 or 2; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In one aspect, $R_1$, $R_3$, and $R_4$ are each independently selected from the group consisting of mono-, bi-, and tri-chloro and mono-, bi, and tri-methyl ($CH_3$).

In accordance with one embodiment, a compound is provided having the structure:

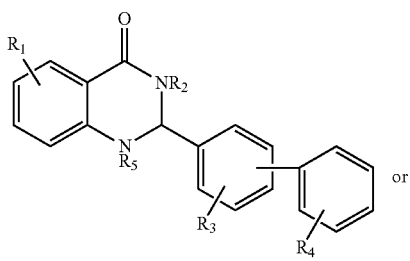

or

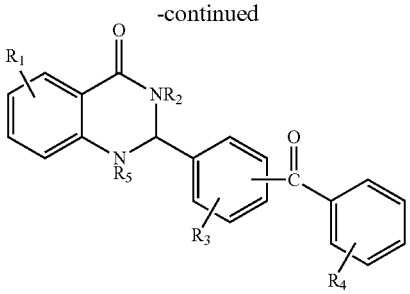

wherein $R_1$, $R_3$ and $R_4$ are independently selected from the group consisting of H, halo and $C_1$-$C_4$ alkyl, and $R_2$ and $R_5$ are independently selected from the group consisting of H, halo, $C_1$-$C_4$ alkyl, and $C_5$-$C_6$ aryl.

Other compounds provide herein include those of the formula:

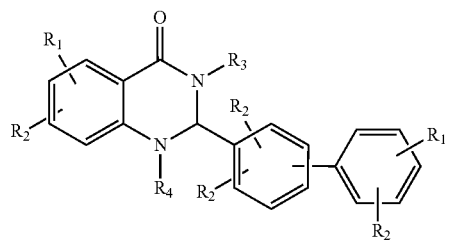

wherein $R_1$ and $R_2$ are independently selected from the group consisting of $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri-chloro and mono-, bi, and tri-methyl ($CH_3$), and $R_3$ and $R_4$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In one embodiment of the invention, a compound has the following general structure:

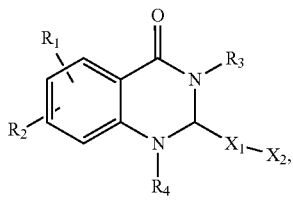

wherein $X_1$ and $X_2$ are each independently selected from the group comprising heterocyclic, including thiophene, pyridine, pyrazine, pyrimidine, thiophene, furan, oxazole, and imidazole, further wherein $X_1$ and $X_2$ may independently comprise $R_1$ and $R_2$.

wherein $R_1$ and $R_2$ are independently selected from the group comprising $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri-chloro and mono-, bi, and tri-methyl ($CH_3$), and $R_3$ and $R_4$ are independently selected from the group comprising H, halo, $C_5$-$C_6$ aryl, $C_1$-$C_4$ alkyl, $C_1$-$C_4$ alkenyl, and $C_1$-$C_4$ alkynyl.

In one embodiment, $X_1$ is thiophene. In one aspect the compound is:

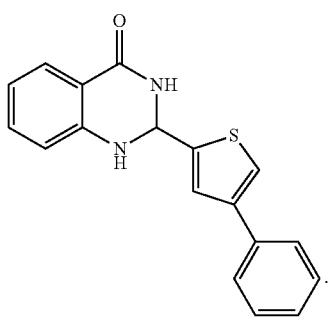 [SMILES: O=C1NC(c2cc(-c3ccccc3)cs2)Nc2ccccc21]

One aspect of the present invention is directed to a method of treating an angiogenic-associated disease or condition by administering a compound or composition that inhibits angiogenesis. More particularly, one embodiment of the present invention is directed to a method of inhibiting undesired angiogenesis in a warm-blooded vertebrate, including humans. In one embodiment the undesired angiogenesis is associated with solid tumors, such as colon cancer. The method comprises the step of administering to the human or animal a composition comprising an effective amount of a compound of the general structure:

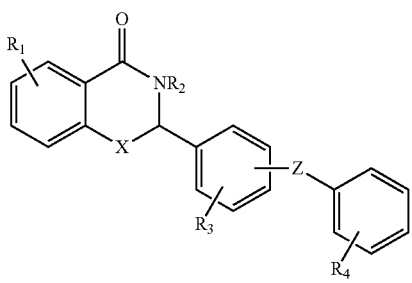

I wherein $R^1$, $R_3$ and $R_4$ are independently selected from the group consisting of H, halo and $C_1$-$C_4$ alkyl or $R_3$ and $R_2$ taken together with the atoms to which they are attached form an optionally substituted heterocyclic fused ring, or $R_3$ and $R_4$ taken together with the atoms to which they are attached form an optionally substituted cycloalkyl fused ring;

X is selected from the group consisting of $NR_5$, —(NH($CH_2$)$_n$)—, $CH_2$, $CHR_5$ and CO; wherein n is 1 or 2;

Z is selected from the group consisting of a bond, O, NH, S, CO, COO, $CH_2$O, $CH_2$NH, CONH, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ allynyl, or $R_3$ and $R_5$ taken together with the atoms to which they are attached form an optionally substituted heterocyclic fused ring.

In one aspect, $R_1$, $R_3$, and $R_4$ are each independently selected from the group consisting of mono-, bi-, and tri-chloro and mono-, bi, and tri-methyl ($CH_3$).

In accordance with one embodiment, the compound of Formula I is provided wherein $R_1$, $R_3$ and $R_4$ are independently selected from the group consisting of H, halo and $C_1$-$C_4$ alkyl;

X is selected from the group consisting of $NR_5$, —(NH($CH_2$)$_n$)—, $CH_2$ and CO; wherein n is 1 or 2;

Z is selected from the group consisting of a bond, O, NH, S, CO, $C_1$-$C_1$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In a further embodiment a compound of Formula I is provided wherein $R_1$, $R_3$ and $R_4$ are independently selected from the group consisting of H, halo and $C_1$-$C_4$ alkyl;

X is selected from the group consisting of $NR_5$, and CO;

Z is selected from the group consisting of a bond, CO and $C_1$-$C_1$ alkyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In one aspect of the invention, compounds of the invention include, but are not limited to:

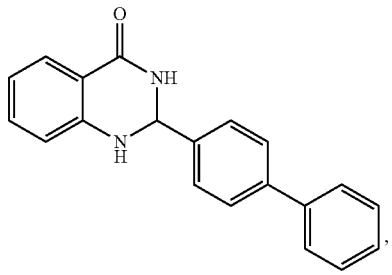

SC-2-71

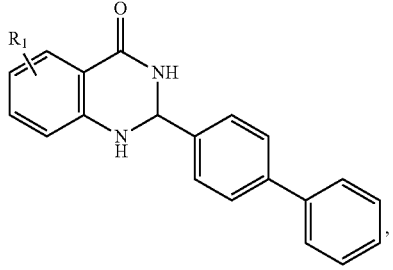

Aryl Substitution (fused ring)

| R1 |
|---|
| 2-Cl, CH3 |
| 3-Cl, CH3 |
| 4-Cl, CH3 |

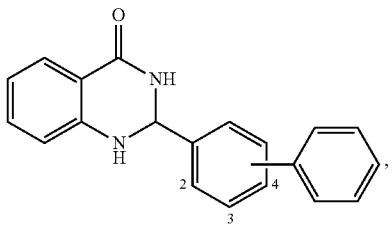

Phenyl Analogues/Isosteres

| |
|---|
| 2-Ph |
| 3-Ph |
| 4-≡ |

-continued
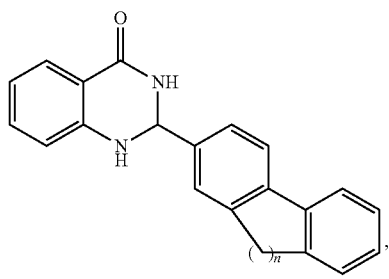
Biphenyl Rigid Analogues
n = 1, 2
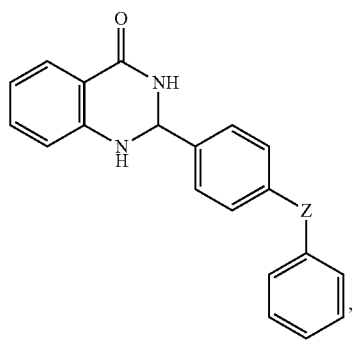
Spacer Insertion
X = CO, CH₂, C₂H₄
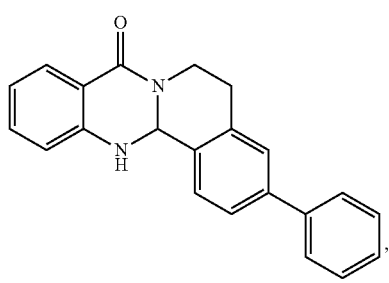
Rigid Analogues
(amide linked)
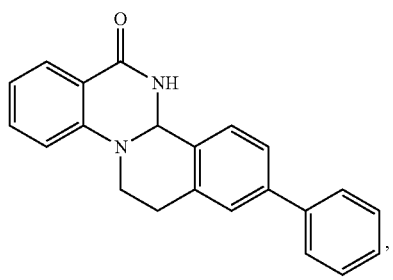
Rigid Analogues (amine)
-continued
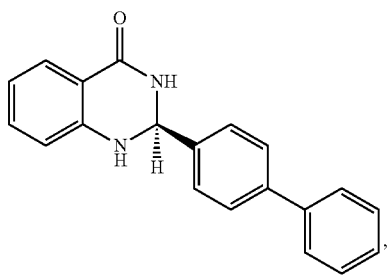
Chiral Analogue
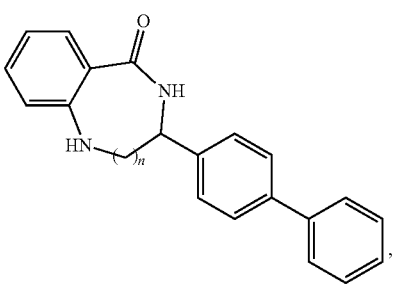
Ring Expansion
n = 1, 2
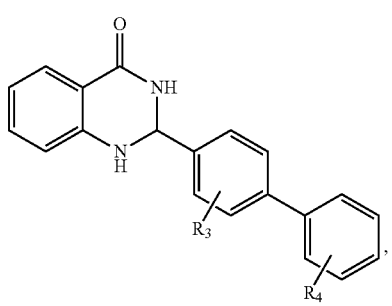
Aryl Substitution (Biphenyl)
| R3 | R4 |
|---|---|
| 2-Cl | H |
| 3-Cl | H |
| 2-CH₃ | H |
| 3-CH₃ | H |
| H | 2,3,4-Cl |
| H | 2,3,4-CH₃ |
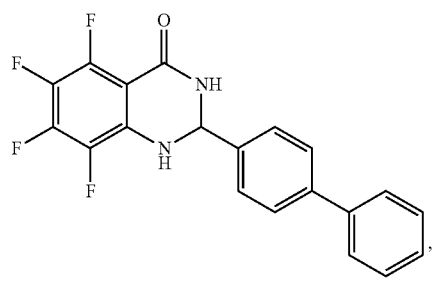
Tetrafluoro -continued

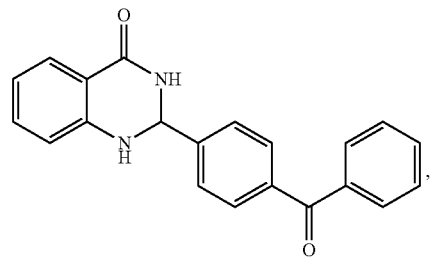 [SMILES: O=C(c1ccccc1)c1ccc(C2NC(=O)c3ccccc3N2)cc1]

,

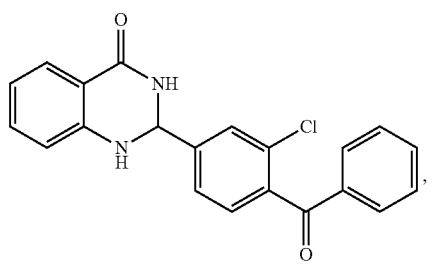 [SMILES: O=C(c1ccccc1)c1ccc(C2NC(=O)c3ccccc3N2)cc1Cl]

,

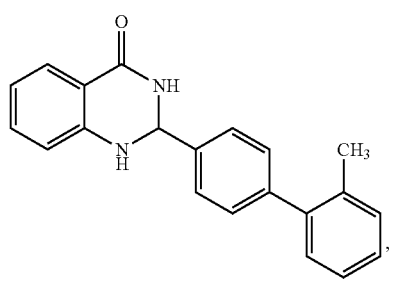 [SMILES: Cc1ccccc1-c1ccc(C2NC(=O)c3ccccc3N2)cc1]

,

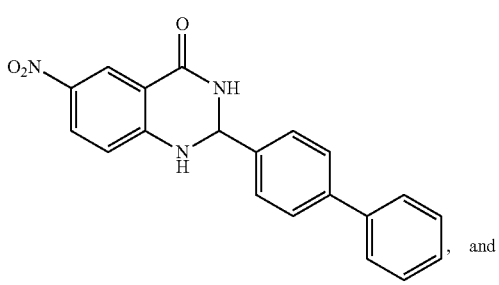 [SMILES: O=C1NC(c2ccc(-c3ccccc3)cc2)Nc2ccc([N+](=O)[O-])cc21]

, and

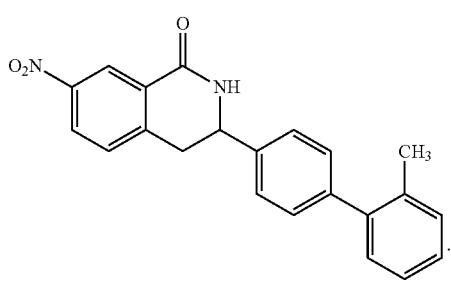 [SMILES: Cc1ccccc1-c1ccc(C2Cc3ccc([N+](=O)[O-])cc3C(=O)N2)cc1]

.

In accordance with one embodiment, the compounds of the present invention can be formulated as pharmaceutical compositions by combining the compounds with one or more pharmaceutically acceptable carriers. These formulations can be administered by standard routes. In general, the combinations may be administered by the topical, transdermal, oral, rectal or parenteral (e.g., intravenous, subcutaneous or intramuscular) route.

When administered orally, the compounds are administered as a liquid solution, powder, tablet, capsule or lozenge. The compounds can be used in combination with one or more conventional pharmaceutical additives or excipients used in the preparation of tablets, capsules, lozenges and other orally administrable forms.

When administered parenterally, and more preferably by intravenous injection, the derivatives of the present invention can be admixed with saline solutions and/or conventional IV solutions. In addition, the combinations may be incorporated into biodegradable polymers allowing for sustained release of the compound, and in one embodiment the delivery vehicle is implanted in the vicinity of where drug delivery is desired, for example, at the site of a tumor. Biodegradable polymers suitable for use with the present invention are known to the skilled practitioner and are described in detail, for example, in Brem et al., J. Neurosurg. 74:441-446 (1991).

The dosage of the active compound will depend on the condition being treated, the particular compound, and other clinical factors such as weight and condition of the human or animal and the route of administration of the compound. It is to be understood that the present invention has application for both human and veterinary use. In one embodiment relating to oral administration to humans, a dosage of between approximately 0.1 to 300 mg/kg/day, or between approximately 0.5 and 50 mg/kg/day, or between approximately 1 to 10 mg/kg/day, is generally sufficient.

It should be understood that in addition to the active anti-angiogenic compounds of Formula I, the compositions of the present invention may include other agents conventional in the art including solubilizing agents, inert fillers, diluents, excipients and flavoring agents.

In accordance with one embodiment a composition comprising a compound of Formula I is used to inhibit angiogenesis. In one embodiment, the composition is administered to treat a disease, disorder, or condition associated with excessive or undesirable angiogenesis, such as that associated with solid tumors. More particularly, microvessel density (MVD) or microvessel count within a tumor is a widely studied marker of angiogenesis. Patients whose tumors have a high MVD have a shorter survival than those with a low MVD. In fact, a correlation of increased microvessel density and poor prognosis has been found for several devastating solid tumors including colorectal cancer (Saclarides et al., Diseases of the Colon & Rectum. 37(9):921-6, 1994).

In one embodiment of the invention, aspect, a compound of the invention is used to inhibit a disease, disorder, or condition which is associated with increased angiogenesis or microvessel density. In accordance with another embodiment, compounds having the general structure of Formula I that exhibit anti-cancer and anti-angiogenic activity, are used to inhibit the growth of solid tumors.

The effects of 123 anticancer agents on the 60 cancer cell lines in the NCI's anticancer drug screen were evaluated for activity against cell lines with wild type or mutant p53 (see examples). Cell lines with mutant p53 were less sensitive to topoisomerase inhibitors, antimetabolites and DNA cross-linkers, as compared to cells with normal p53. The one group of chemotherapeutic agents that differed in this regard included anti-microtubule agents. These in vitro results are consistent with clinical results (Safran, et al., Cancer, 78: 1203-1210, 1996). Thus, it is anticipated that the compounds of Formula I may have enhanced efficacy against cancers that express an altered p53.

The compounds of the present invention are useful as anti-proliferative agents against cancer cells. In one aspect, the cancer cells include, but are not limited to, colon, multiple myeloma, breast, leukemia, cervical, central nervous system, non small cell carcinoma, melanoma, ovarian, and prostate cancer cells. In one aspect, the cancer is a solid tumor. In another aspect, the cancer is a leukemia.

The effectiveness of the compounds of the invention in inhibiting tumor growth can be measured by numerous techniques known to those of skill in the art. Such techniques include the use of radiolabeled compounds, numerous radiographic imaging techniques, as well as physical measurement.

In one embodiment, the compounds of the invention are administered to a subject in a pharmaceutical composition further comprising a known chemotherapeutic agent. Chemotherapeutic agents are known to those of ordinary skill in the art, as are the doses to be used.

Another disease which can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

The compounds of the present invention are also anticipated to have use in treating a wide variety of diseases or conditions that are related to angiogenesis, including diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, pemphigold radial keratotomy, and corneal graph rejection. In another embodiment, diseases associated with corneal neovascularization can be treated by administering a composition comprising a compound of Formula I. Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitreitis, mycobacterial infections, Lyme's disease, systemic lupus erythematosus, retinopathy of prematurity, Eales' disease, Behcet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications.

The compounds of Formula I as described herein have been found to exhibit anti-microtubule activity.

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art. For example, a pharmaceutical composition comprising a compound of the invention, or analog, derivative, or modification thereof, as described herein, is used to administer the appropriate compound to a subject.

Pharmaceutical compositions comprising the a compound of the invention are administered to a subject in need thereof by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the compounds of the invention. Preference is given to intravenous injection or infusion for the acute treatments. For maintenance regimens, the oral or parenteral, e.g. intramuscular or subcutaneous, route is preferred.

In accordance with one embodiment, a composition is provided that comprises a compound of the invention, or an analog, derivative, or modification thereof, and albumin, more particularly, the composition comprises a compound of the present invention, a pharmaceutically acceptable carrier and 0.1-1.0% albumin. Albumin functions as a buffer and improves the solubility of the compounds. In one aspect, albumin is not added.

In one embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 100 g/kg/day.

Pharmaceutically acceptable carriers which are useful include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides.

Compounds which are identified using any of the methods described herein may be formulated and administered to a subject for treatment of any of the diseases and disorders described herein. However, the use of compounds of the invention should not be construed to include only the diseases and disorder described herein. Preferably, the subject is a human.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals, including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed by the present invention.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. See Genaro, ed., 1985, Remington's Pharmaceutical Sciences, Mack Publishing Co., Easton, Pa., which is incorporated herein by reference.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type, and age of the subject, etc.

The invention also provides a pharmaceutical pack or kit comprising one or more containers filled with one or more of the ingredients of the pharmaceutical compositions of the invention. In accordance with one embodiment, a lit is provided for treating a subject in need of immuno-modulation. Preferably, the subject is a human. In one embodiment, the kit comprises one or more of the S1P analogs of the present invention and may also include one or more known immuno-suppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Although any methods and materials similar or equivalent to those described herein can be used in the practice or testing of the present invention, the preferred methods and materials are described herein.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Example 1

SC-2-71 Effects on Proliferation

SC-2-71 was evaluated against human cultured cell lines in the NCI Anticancer Drug Development Program. The data provided below in Table 2 reveals that SC-2-71 is a potent inhibitor of colon cancer proliferation with anti-proliferative activities ranging from 68 nM to 4 µM. This includes potent inhibition of colon cancer cells from primary tumors, distal metastasis and ascites fluid.

TABLE 2

$GI_{50}$ summary for human colon cell lines treated with SC-2-71.

| Compound | $GI_{50}$ Data (µM) | | | | | | |
|---|---|---|---|---|---|---|---|
| | HT29 | COLO205 | HCC-2998 | HCT-116 | HCT-15 | KM12 | SW-620 |
| SC-2-71 | 1 | 0.9 | 0.068 | 0.5 | 0.4 | 2 | 4 |
| Vincristine[a] | 0.11 | 0.12 | 0.11 | 0.12 | 0.14 | 0.12 | 0.11 |
| 5FU[a] | 6.7 | 7.2 | 1.4 | 4.0 | 5.8 | 11.1 | 26.2 |

[a]NCI data. 5FU = 5-Fluorouracil

Further grade III tumor cells (HCT116) were also significantly inhibited (GI$_{50}$=500 nM). In comparison to 5-FU (currently approved for stage III colon cancer), SC-2-71 was significantly more effective at inhibiting human colon cancer cell lines. SC-2-71 had similar potency as compared to Vincristine, a well known anti-mitotic agent. Altogether, this data establishes that SC-2-71 has therapeutically relevant anti-proliferative activity against human cultured colon cancer cells.

Furthermore, as indicated by the GI$_{50}$ data obtained from the National Cancer Institute (NCI) and presented in FIG. 1, SC-2-71 also exhibits toxicity to a wide range of tumor cell lines. The smallest bars represent the cell lines for which SC-2-71 had the most potent anti-proliferative effect. Several interesting findings are evident. First, SC-2-71 can potently inhibit several types of cancers in the nanomolar range (the lowest GI$_{50}$ (colon HCC2998)=68 nanomolar). Second, the differential response to SC-2-71 by the cancer cell lines demonstrates that SC-2-71 is not toxic to every cell type (i.e. several GI$_{50}$'s are greater than 100 μM). Third, SC-2-71 does not have to be metabolically activated like thalidomide to have anti-cancer activity, since it is directly toxic when applied to cancer cells.

Figure 2A:
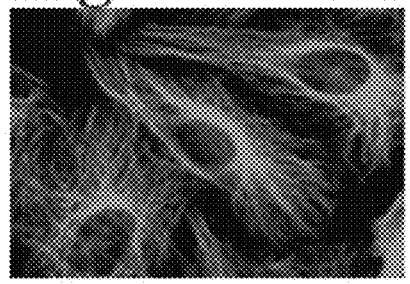
FIG. 2 Depicts the microtubule depolymerizing effects of SC-2-71 in A-10 cells.
Figure 2B:
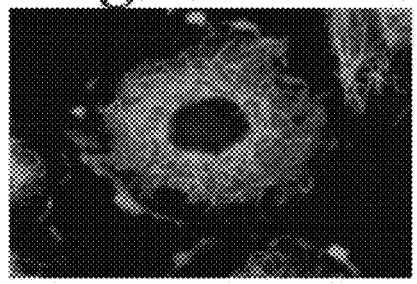

The microtubule disrupting effects of SC-2-71 were detected in a cell based phenotypic screen (FIG. 2). SC-2-71 was observed to cause dramatic reorganization of the interphase microtubule network, similar to the effects of vinblastine. While vehicle treated cells exhibit a normal filamentous microtubule array (FIG. 2), SC-2-71 caused a concentration dependent loss of cellular microtubules. This effect is consistent with the effects observed from other microtubule depolymerizers. In addition to microtubule loss, treatment of the cells with SC-2-71 resulted in extensive micronucleation. This is also a hallmark of microtubule disrupting compounds. Depolymerization of interphase microtubules is a classic response of cells to relatively high concentrations of microtubule disruptors such as the vinca alkaloids. However, a large body of evidence suggests that at the lowest effective cytotoxic concentrations, the ability of these compounds to interrupt normal microtubule dynamics (and not changes in the tubulin polymer) causes mitotic arrest and subsequent apoptosis (Jordan, M. A., Curr. Med. Chem. 2:1-17, 2002).

Figure 3A:
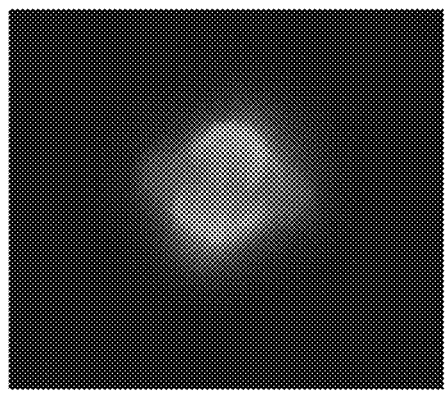
FIG. 3 Demonstrates abnormal mitotic spindles initiated by low micromolar concentrations of SC-2-71 in HeLa cells.
Figure 3B:
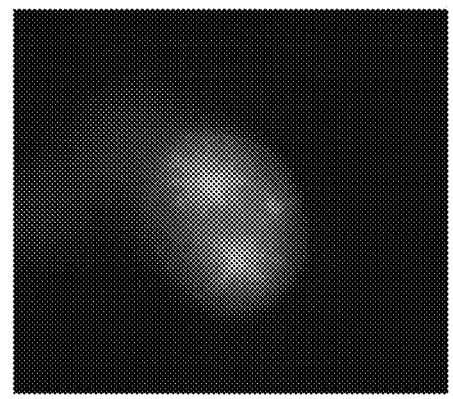

The ability of SC-2-71 to initiate mitotic accumulation and the formation of abnormal mitotic spindles was evident in both A-10 and HeLa cells at concentrations that did not cause dramatic changes in interphase microtubules. In HeLa cells, SC-2-71 causes the formation of abnormal mitotic spindles and mitotic accumulation at low micromolar concentrations (FIG. 3).

The effects of SC-2-71 on cell cycle progression were determined using flow cytometry techniques. MDA-MB-435 cells were treated with 3 μM SC-2-71 for 18 h, stained with Krishan's reagent and DNA content analyzed. The results (FIG. 4) show distinct mitotic accumulation consistent with interruption of normal mitotic spindle function and mitotic arrest.

The anti-proliferative activity of SC-2-71 as shown in table 4 was evaluated using the SRB assay and it was found to have good potency against a reference cell line, MDA-MB-435. Analogues of SC-2-71 were tested for the ability to disrupt microtubules and for potency against MDA-MB-435. These tubulin depolymerization studies revealed that SC-2-71 potently inhibited tubulin polymerization (50% at 5 μM). The activities of several analogues of SC-2-71 that have microtubule disrupting activity, as defined by greater than 50% microtubule loss at 30 μM, are presented in Table 4. The data indicates that certain derivatives of SC-2-71 have even higher anti-microtubule activity (see compounds SC-5-87 and SC-5-121).

TABLE 4

Effects of analogues on Pgp expressing cells and tubulin polymerization.

| Compound | MDA-MB-435 Cells (IC$_{50}$ μM) | NCI/ADR Cells (Pgp expressing) (IC$_{50}$ μM) | Rr value | Microtubule activity (% depolymerization) |
|---|---|---|---|---|
| SC-2-71 | 0.61 ± 0.1 | 1.80 ± 0.11 | 2.95 | 50% at 5 μM |
| SC-4-283 | 0.90 ± 0.3 | | | 50% at 5 μM |
| HAMEL4 | 1.95 ± 0.4 | 3.19 ± 0.23 | 2.0 | 50% at 5 μM |
| SC-5-87 | 0.26 ± 0.02 | 0.76 ± 0.01 | 2.9 | 90% at 5 μM |
| SC-5-121 | 0.6 ± 0.1 | 0.88 ± 0.03 | 1.2 | 90% at 5 μM |

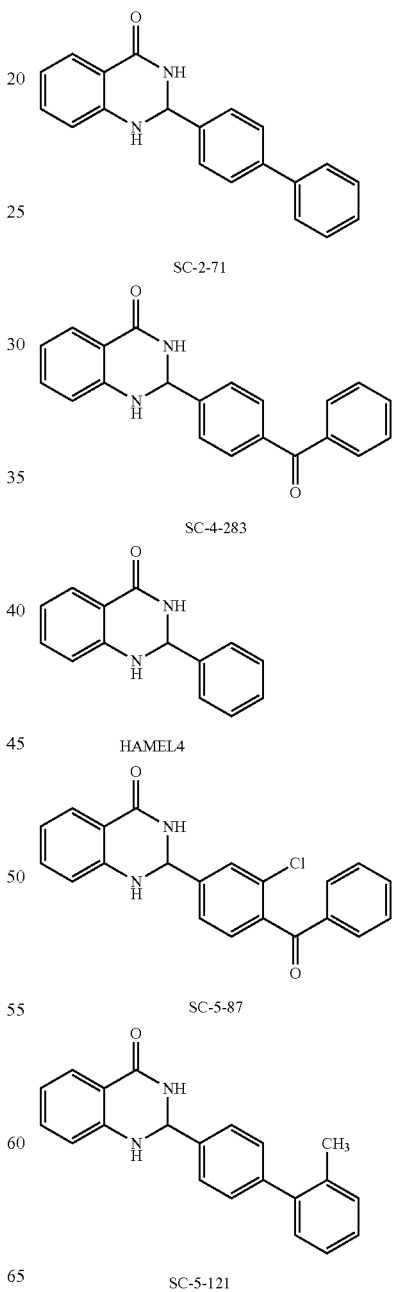

The ability of anti-microtubule/anti-angiogenesis compounds to circumvent Pgp may provide significant advantages for therapy of drug resistant tumors. The ability of SC-2-71 analogues to inhibit the proliferation of the Pgp expressing cell line NCI/ADR is demonstrated by the data provided in Table 4. Relative resistance (Rr) values can be calculated by dividing the $IC_{50}$ of the sensitive cell line by the $IC_{50}$ of the resistant cell line. The Rr value for taxol in the NCI/ADR (Pgp expressing) and MDA-MB-435 (Pgp deficient) cell lines is 827 (Tinley, et al., Cancer Res. 63:1538-1549, 2003b). The Rr values for the present SC-2-71 analogues range from 1.3 to 2.9 strongly suggesting that they are poor substrates for transport by Pgp, and thus should be more effective agents against Pgp mediated multi-drug resistance.

Example 2

Comparative Molecular Field Analysis (CoMFA) of SC-2-71 and Tubulin Polymerization CoMFA is a powerful ligand based discovery methodology to identify important relationships between steric and electrostatic molecular properties and biological data. A β-tubulin CoMFA has been developed that resulted in models which were predictive of both tubulin polymerization and [$^3$H] colchicine binding for a large set of β-tubulin inhibitors (Brown, et al., Bioorganic and Medicinal Chemistry, 8:6: 1433-1441, 2000). This study produced the first predictive models for multiple structural types including combretastatins, colchicine and podophyllotoxin. More recently, this CoMFA model was used to identify and predict the β-tubulin depolymerization activity of SC-2-71. The CoMFA model predicted that SC-2-71 would be a potent inhibitor of tubulin polymerization as was previously reported for the parent HAMEL4 compound (Hour et al., Journal of Medicinal Chemistry, 43:23:4479-87, 2000).

SC-2-71 Inhibits β-Tubulin Polymerization

Analogues of SC-2-71 were tested for the ability to disrupt microtubules, and for potency against MDA-MB-435. These tubulin depolymerization studies revealed that SC-2-71 potently inhibited tubulin polymerization (50% at 5 μM). The activities of several analogues of SC-2-71 that have microtubule disrupting activity, as defined by greater than 50% microtubule loss at 30 are presented in Table 4. The data indicates that certain derivatives of SC-2-71 have even higher anti-microtubule activity (see compounds SC-5-87 and SC-5-121).

It is believed that the anti-proliferative activity of the responding cell lines to SC-2-71 treatment is due to a difference in tubulin isotype expression in the responding cells. In fact, a proteomic study revealed that class III tubulin (βIII) is upregulated in HT29 colon cancer cells (Braguer et al., British Journal of Cancer, 80(8):1162-8, 1999). This cell line was very sensitive to SC-2-71 ($GI_{50}$=1 μM).

Example 3

Investigating the SC-2-71 Mechanism of Action

Figures 4, 5:
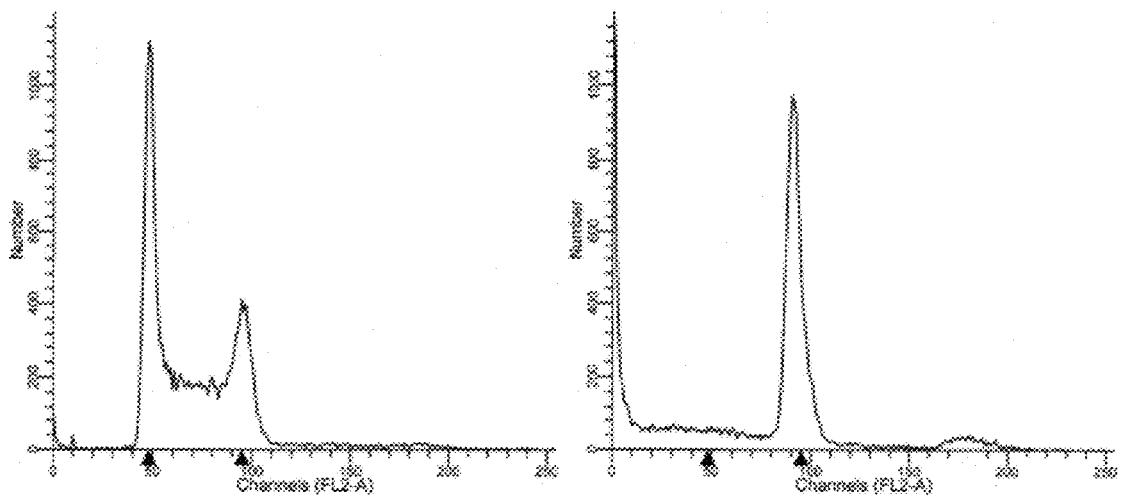
FIG. 4 Depicts flow cytometric studies of MDA-MB-435 with treated with 3 µM SC-2-71.
FIG. 5 Demonstrates a sequence alignment of βIII tubulin with the known x-ray structure (SEQ ID NOs:1-2).
Figure 6A:
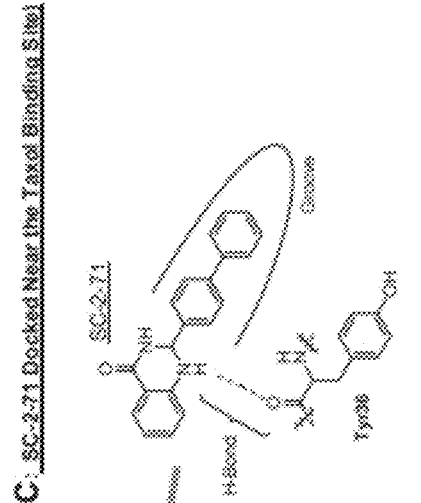
FIG. 6 Demonstrates the docking of SC-2-71 into the βIII homology model.
Figure 6B:
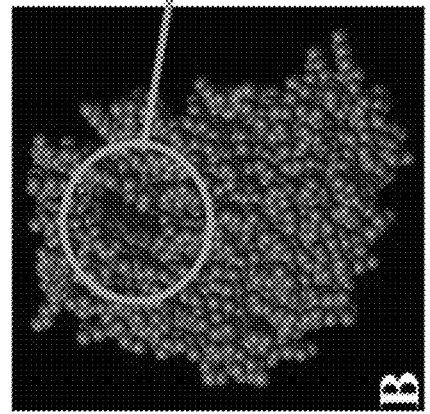
Figure 6C:
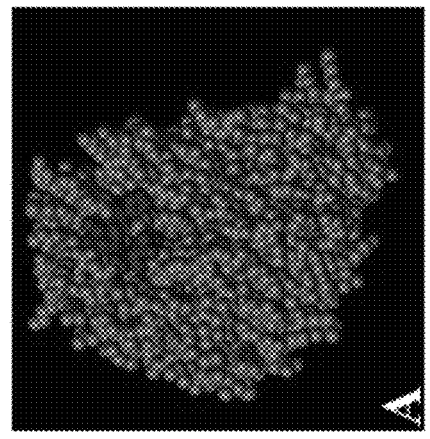

A 96% sequence homology (identity) exists between the x-ray structure sequence of β-tubulin (bovine brain) and βIII (human) (see FIG. 5). With this high level of homology, we embarked on developing a protein model of human βIII (FIG. 6B). Using the BIOPOLYMER module within SYBYL we threaded the sequence in FIG. 5 into the reported x-ray structure to create the homology model of βIII human tubulin (FIG. 6). We then took our homology model of βIII and flexible docked SC-2-71 into it using the FlexX/C-Score module within SYBYL (FlexX was developed at the German National Research Center for Information Technology (GMD), and is distributed by Tripos Inc., St. Louis Mo.; ww.tripos.com/software/flexx.html). SC-2-71 docks right into the area of greatest amino acid difference near the taxol and colchicine binding sites (FIG. 6). Overlap of the homology with the x-ray structure revealed that changes in amino acids resident in the PHI protein near the taxol and colchicine binding sites could impart selective binding to SC-2-71. One important hydrogen bond was noted between tyrosine 36 and the amine portion of SC-2-71. Comparison of predicted binding affinities to βIII tubulin suggested the rank order of SC-4-283 >SC-2-71. This order was experimentally confirmed by tubulin depolymerization experiments in Table 4.

Figure 7:
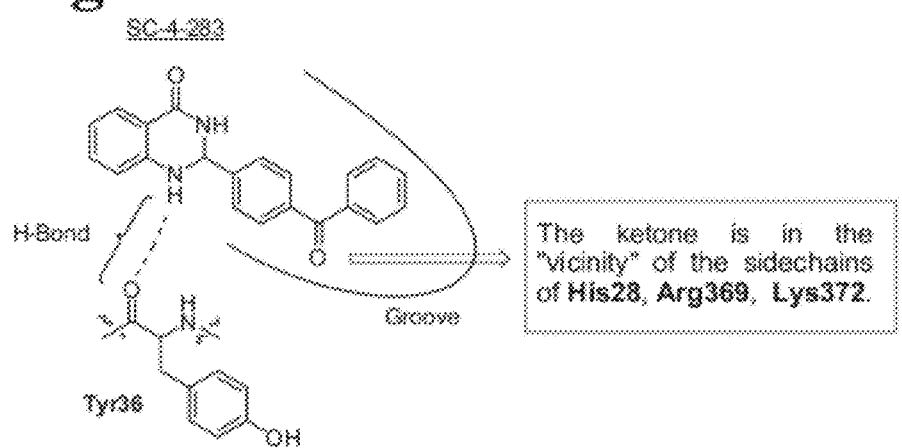
FIG. 7 Demonstrates the flexible docking of the potential photoaffinity label SC-4-283.

The model described herein was used to customize and design SC-4-283, a potential photoaffinity ligand of SC-2-71 (FIG. 7). The ketone is within a few angstroms of the sidechains of His28, Arg369, and Lys372. Therefore, these amino acids may provide potential reaction sites for imine formation. With this in mind, we synthesized SC-4-283 as a benzophenone photoaffinity label of SC-2-71 in an effort to elucidate and confirm the binding domain of SC-2-71. We evaluated SC-4-283 for inhibition of tubulin polymerization and found it to have improved inhibitory activity in relation to SC-2-71 (Table 4) as we predicted. Our model has allowed us to 1) to assign priority of synthesis to our new ligands based on rank of the ligand's predicted affinities to β-tubulin and 2) design potential affinity labels and 3) propose labeling, digest and sequence analysis to validate our hypothesis.

Example 4

Inhibitory Effects of SC-2-71 on Endothelial Cell Proliferation In Vitro and In Vivo Without wishing to be bound by any particular theory, strategies and experiments' are described herein pertaining to developing an anti-cancer strategy of simultaneously inhibiting endothelial and cancer cells. Compounds that target cellular microtubules have recently been found to exhibit anti-angiogenic activities and this may contribute to their antitumor and anticancer efficacies (Miller, et al., J. Clin. Oncol. 19:1195-1206, 2001). The taxanes, taxol and docetaxel, vinblastine, vincristine and 2-methoxyestradiol all have anti-angiogenic activity in vivo. SC-2-71 inhibited Human Microvessel Endothelial Cell (HMEC; $IC_{50}$ of 20 μM) and Human Umbilical Vein Endothelial Cells (HUVEC; $IC_{50}$ of 1.6 μM) proliferation (see Table 5). SC-2-71's ability to inhibit angiogenesis in an in vivo model was then examined.

TABLE 5

Inhibitory effects of SC-2-71 on endothelial cell proliferation.

| Compd | HMEC[b] $IC_{50}$ (μM) | HUVEC[c] $IC_{50}$ (μM) |
|---|---|---|
| SC-2-71 | 20 ± 5 | 1.66 ± 0.5 |

[a]All experiments were run in triplicate, and the ± values represent the SEM
[b]Human Microvessel Endothelial Cells
[c]Human Umbilical Vein Endothelial Cells SC-2-71 Inhibits the Growth of Blood Vessels on the Chick Chorioallantoic Membrane (CAM) Model.

Figure 8A:
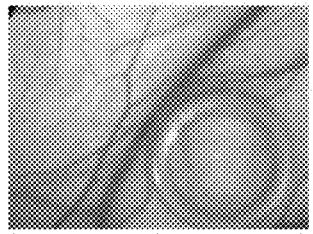
FIGS. 8A-C SC-2-71 (100 µM) inhibited a translational model of blood vessel growth in vivo (CAM, panels B and C) as compared to control (panel A).
Figure 8B:
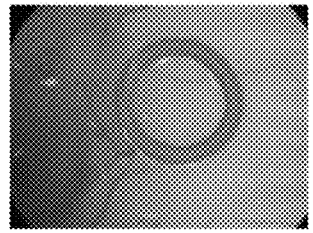
Figure 8C:
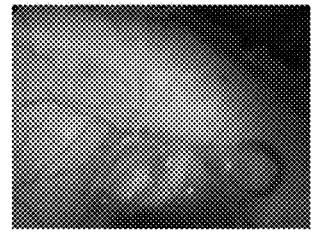

SC-2-71 (100 μM) inhibited a translational model of blood vessel growth in vivo (CAM, FIG. 8, panel B and C) as compared to control (FIG. 8, panel A). This strongly establishes that SC-2-71 has anti-angiogenic activity. Further it raises the question as to the expression level of βIII tubulin in HMECs.

A summary of the results obtained with SC-2-71 is as follows:

1) SC-2-71 is a potent inhibitor of colon cancer proliferation with anti-proliferative, activities ranging from 68 nM to 4 μM;

2) In comparison to 5-FU (currently approved for stage III colon cancer), SC-2-71 was significantly more effective at inhibiting human colon cancer cell lines;

3) SC-2-71 is a microtubule depolymerizing agent;

4) SC-2-71 caused dramatic reorganization of interphase microtubule networks, similar to the effects of vinblastine;

5) SC-2-71 causes the formation of abnormal mitotic spindles and mitotic accumulation at low micromolar concentrations;

6) SC-2-71 was a poor substrate for transport by Pgp;

7) A homology model of βIII human tubulin was developed and used to 1) prioritize synthesis and 2) design a potential photoaffinity label.

8) SC-4-283 was synthesized as a benzophenone photoaffinity label of SC-2-71 and found to also be a potent inhibitor of tubulin polymerization.

9) SC-2-71 inhibits the proliferation of human microvessel and umbilical vein endothelial cells.

10) SC-2-71 inhibits the growth of blood vessels in an in vivo model of angiogenesis.

Example 5

Synthesis of SC-2-71 and Derivative Compounds

SC-2-71 and analogues were synthesized in accordance with the following schemes by condensing anthranilamide with an appropriately substituted benzaldehyde derivative as shown in Scheme 1. Recrystallization of the crude solids from absolute ethanol afforded the pure products listed.

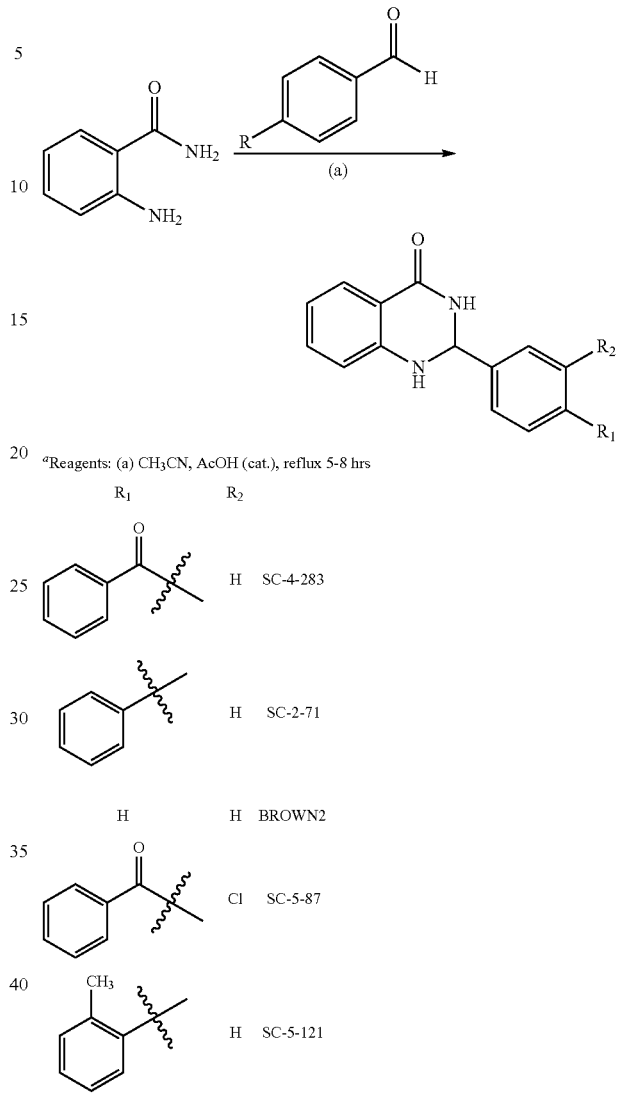

Scheme 1. Synthetic route for SC-2-71 and analogues.

[a]Reagents: (a) $CH_3CN$, AcOH (cat.), reflux 5-8 hrs

Compounds designed to optimize SC-2-71.

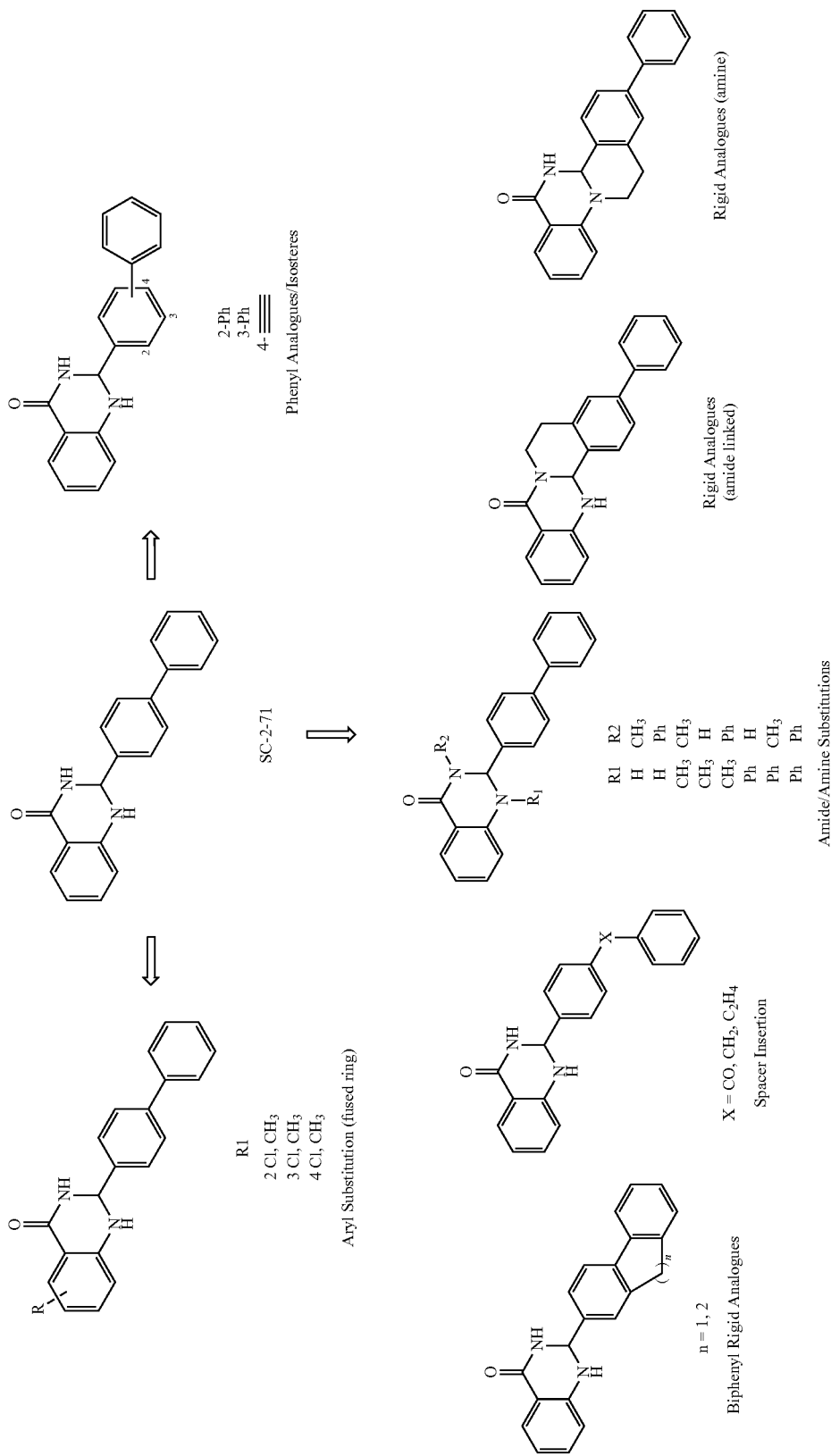

-continued
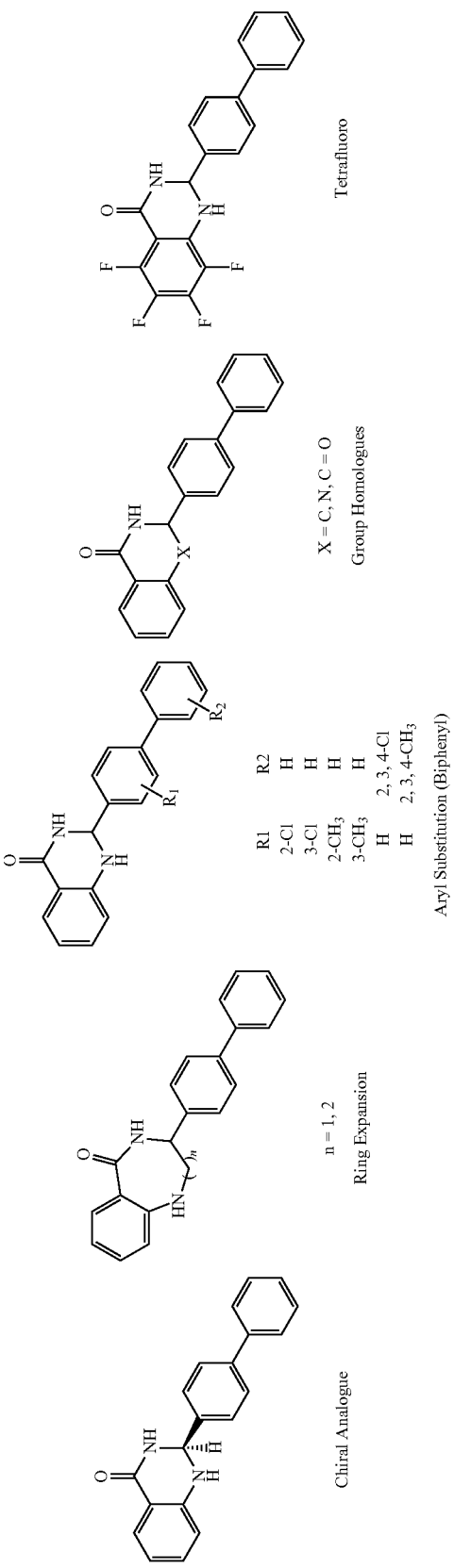

Other compounds include:

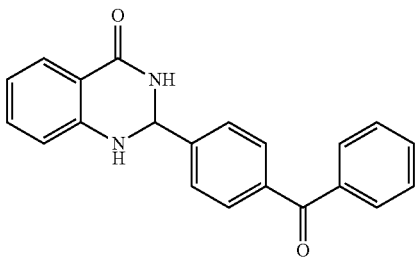

SC-4-283
m.p. = 209-211° C.
¹H NMR, ¹³C NMR, NCI: Declined

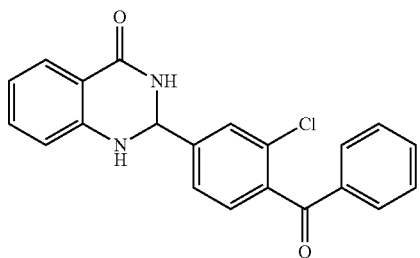

SC-5-87
m.p. = 177-179° C.
¹H NMR, ¹³C NMR, NCI: 60-cell ,

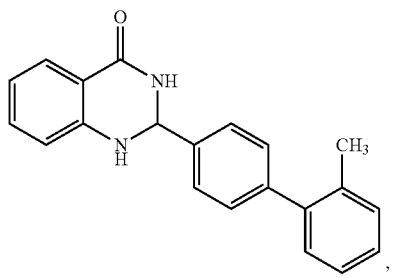

SC-5-121
m.p. = 169-171° C.
¹H NMR, ¹³C NMR, NCI: 60-cell

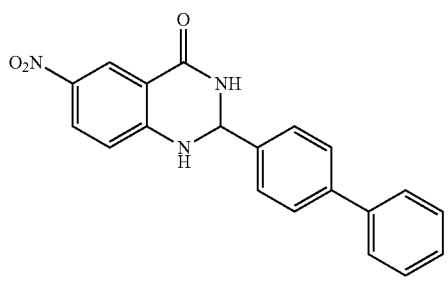

GMC-5-93
m.p. = 263-265° C.
¹H NMR, ¹³C NMR, NCI: Declined ,

-continued

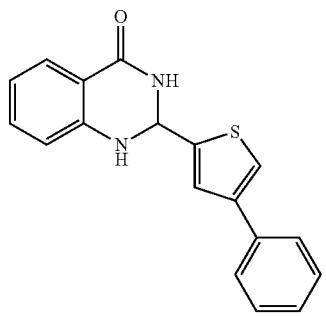

GMC-5-103
m.p. = 228-230° C.
¹H NMR, ¹³C NMR, NCI: , and

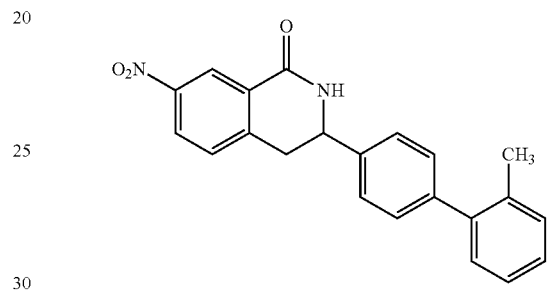

GMC-5-193
m.p. = 251-252° C.
¹H NMR, ¹³C NMR, NCI: 60-cell .

The compounds described above also all have compelling in vitro data demonstrating their effects against colon and breast cancer. Each compound described herein is also a potent tubulin inhibitor and displaces ³H-colchicine (data not shown).

Many of the starting aldehydes needed to complete the synthesis of the analogues of SC-2-71 are not commercially available. A brief outline of the synthesis of several of these important intermediates is provided below.

Scheme 2.

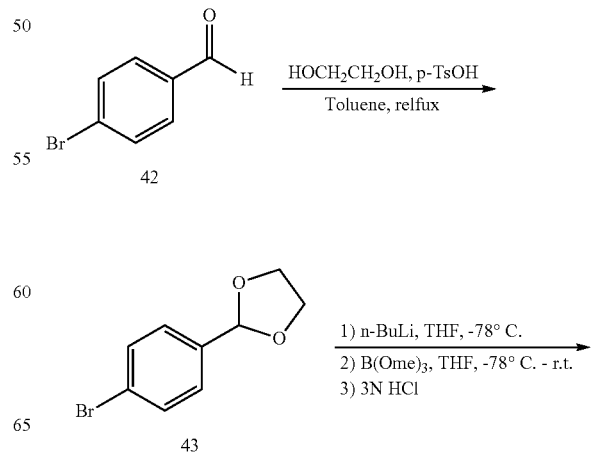

-continued

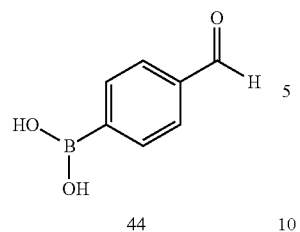

44

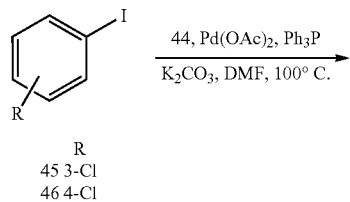

R
45 3-Cl
46 4-Cl

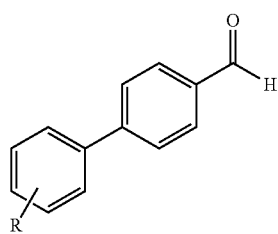

R
47 3-Cl
48 4-Cl

Example 6

Other Syntheses

A method for synthesis of the important synthetic intermediate 4-formylphenylboronic acid 44 with an acetal protection of 4-bromobenzaldehyde 42 is proposed. The resulting acetal will be converted to the trimethylborate and deprotected to afford the boronic acid 44. Key aldehydes 47 and 48 will be obtained under Suzuki coupling conditions using 44 and the appropriate substituted iodobenzene (Scheme 2).

Scheme 3.

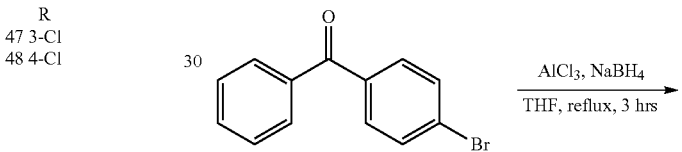

49

50

-continued

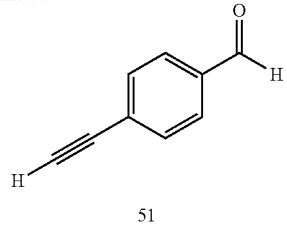

51

The synthesis of 4-ethynylbenzaldehyde 51 using a modified Castro-Stephens/Sonogashira coupling of 4-iodobenzaldehyde and trimethylsilylacetylene (Scheme 3) is proposed. Treatment of this aldehyde with potassium carbonate in methanol at room temperature should afford aldehyde 51. The plan for the synthesis of aldehyde 57 (4-benzoylbenzaldehyde) involves reducing 4-bromobenzophenone 52 and protecting the resulting secondary alcohol 53 with TBS to give 54. After the formylation of 54, we will deprotect and oxidize 56 to the final aldehyde 57 (Scheme 4). In this same manner, we plan to install a formyl group onto the aryl bromide 58 to give 59 (Scheme 5).

Scheme 4.

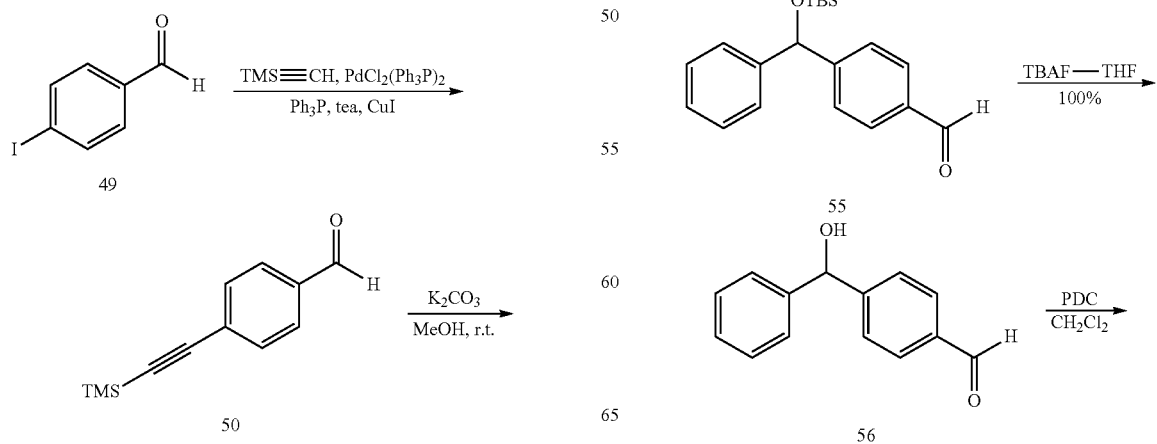

-continued

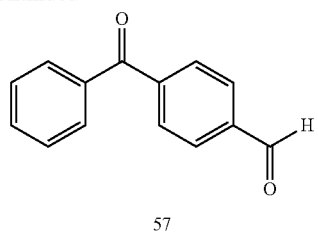

57

-continued

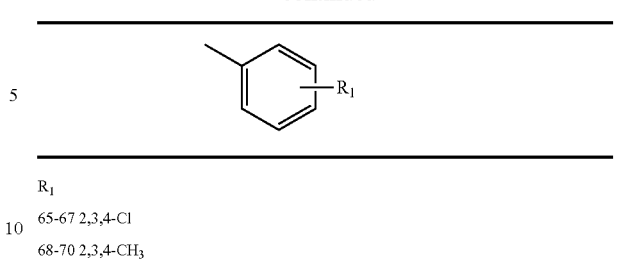

| R₁ |
|---|
| 65-67 2,3,4-Cl |
| 68-70 2,3,4-CH₃ |

Synthesis of these analogues will be accomplished using the same procedure described for SC-2-71 (Scheme 1). It will also require the condensation of the appropriate aldehyde (as outlined in above sections).

Scheme 5.

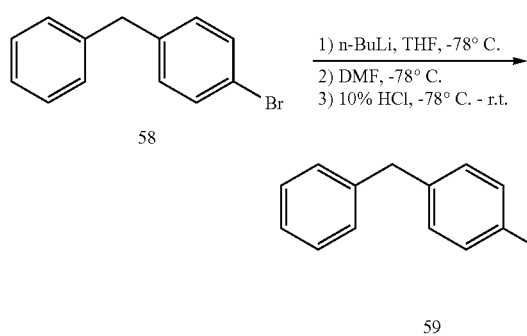

Scheme 7. Synthesis of unsaturated quinazolinones

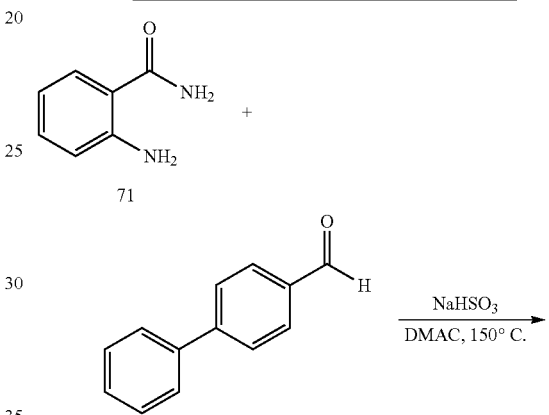

Scheme 6. Synthesis of second generation analogues 62-70.

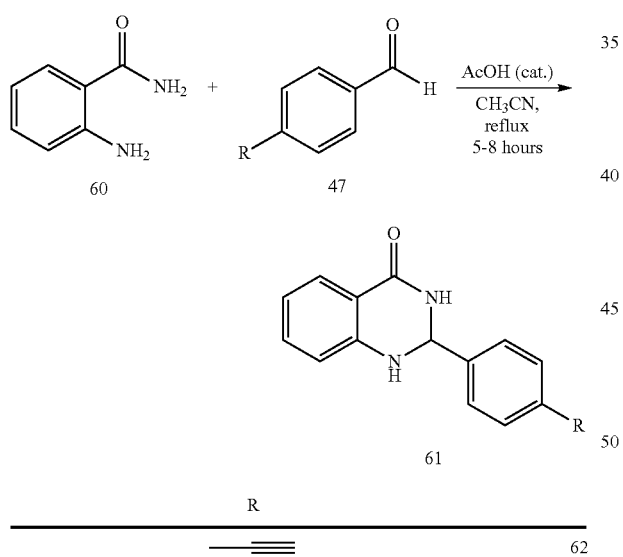

| R |
|---|
| 62 —≡ |
| 63 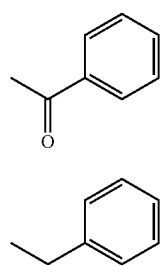 |
| 64 ethyl-phenyl |

A one pot condensation reaction of anthranilamide 71 with 4-biphenylcarboxaldehyde 72 is envisioned to accomplish this synthetic target (Scheme 7). This reaction would be highly adaptable to derivatization.

Scheme 8. Synthesis of tetrafluoroquinazolinone

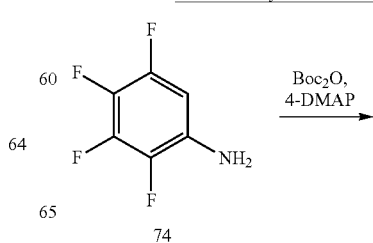

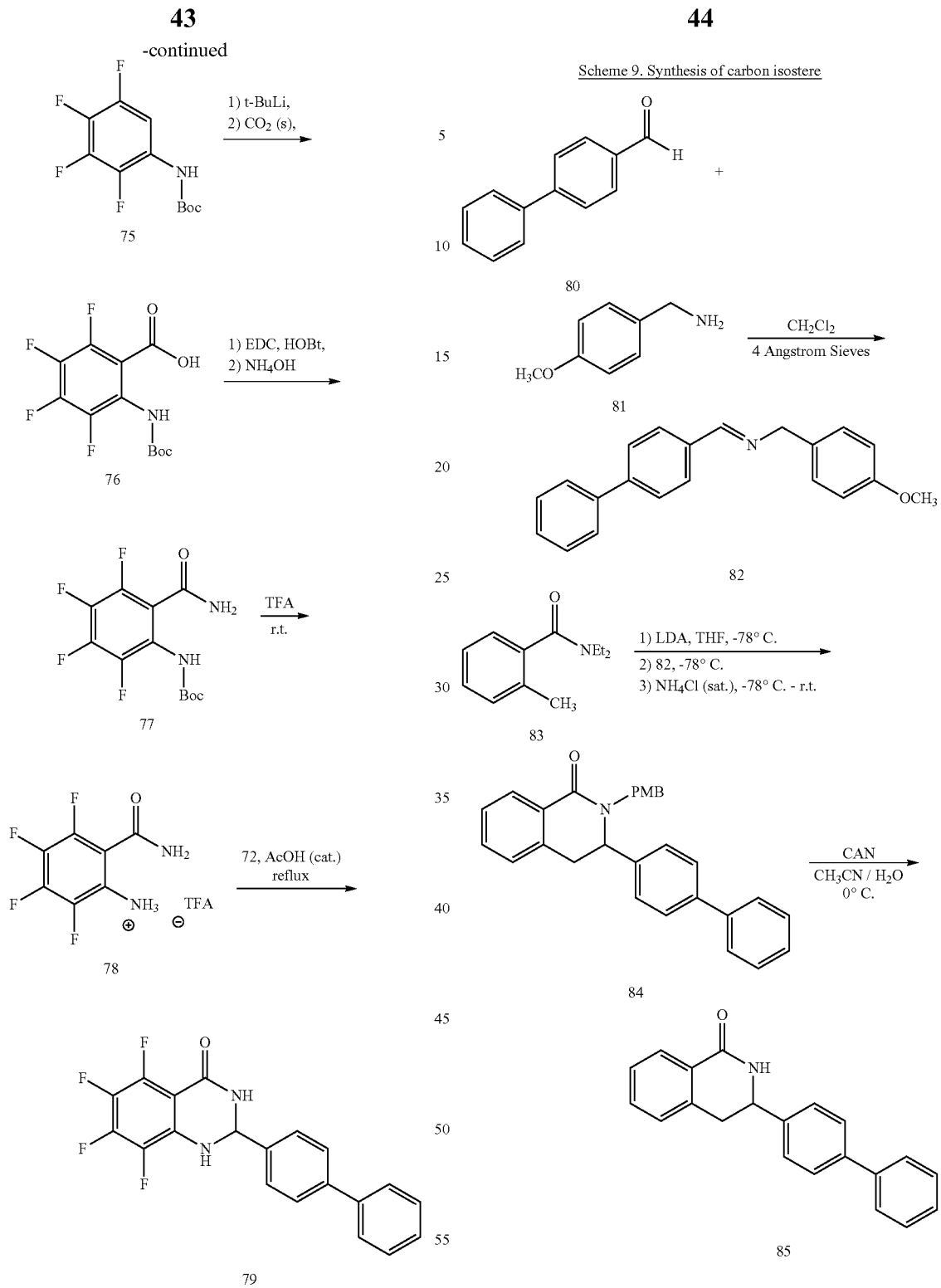

The Tetrafluoroquinazolinone 79, will be synthesized using a lateral ortholithiation of the Boc protected amine 75 (Scheme 8). Following lithiation, we will form 76 from the addition of a slurry of solid carbon dioxide in THF. This will afford the desired protected anthranilic acid derivative 76. The resulting carboxylic acid will be converted to the amide 77 and condensed with 4-biphenylcarboxaldehyde to give the final compound 79.

The carbon isostere of SC-2-71 will be synthesized through an imine condensation strategy (Scheme 9). This will involve forming the appropriate imine 83. Addition of 83 to the N,N-diethyl-2-methylbenzamide 83 will give the PMB protected amide 84. Deprotection with aqueous CAN (ceric ammonium nitrate) will afford the final product 85. This compound will be useful in further elucidating the importance of the amine nitrogen in our proposed NH-tyrosine 36 interaction.

Scheme 10. Synthesis of rigid analogues (amine)

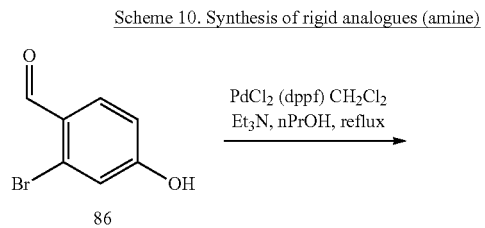

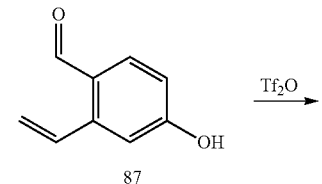

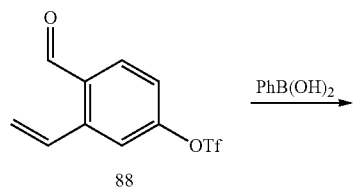

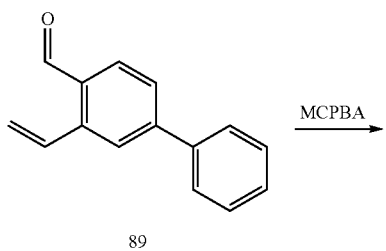

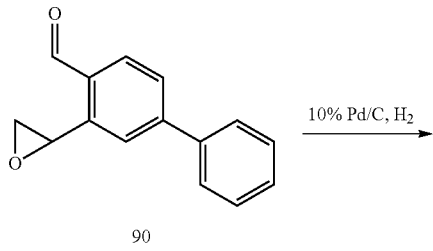

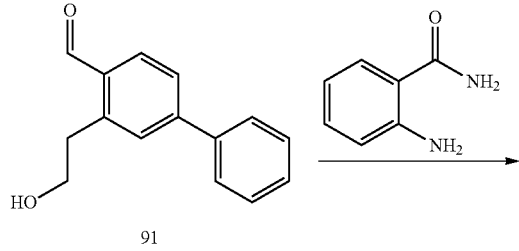

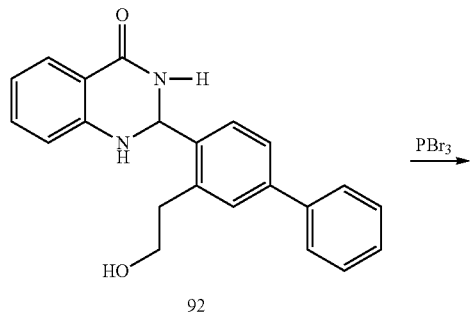

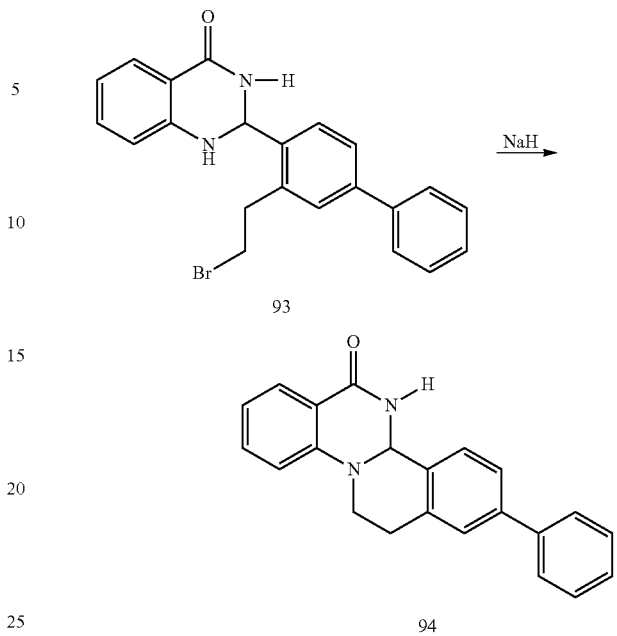

To synthesize rigid analogue 94 (Scheme 10), the addition of an allylic group to 86 will be accomplished by a palladium coupling reaction. The substituted phenol 87 will be triflated and then the biphenyl 89 will be preparation for a standard Suzuki coupling: Addition of MCPBA will give the epoxide 90. This will be ring opened to generate the alcohol 91. Condensation of 91 with anthranilimide will afford 92. Bromination of the alcohol with PBr3 will generate 93. Cyclization of 93 will provide the final product 94.

Scheme 11. Synthesis of rigid analogues (amide).

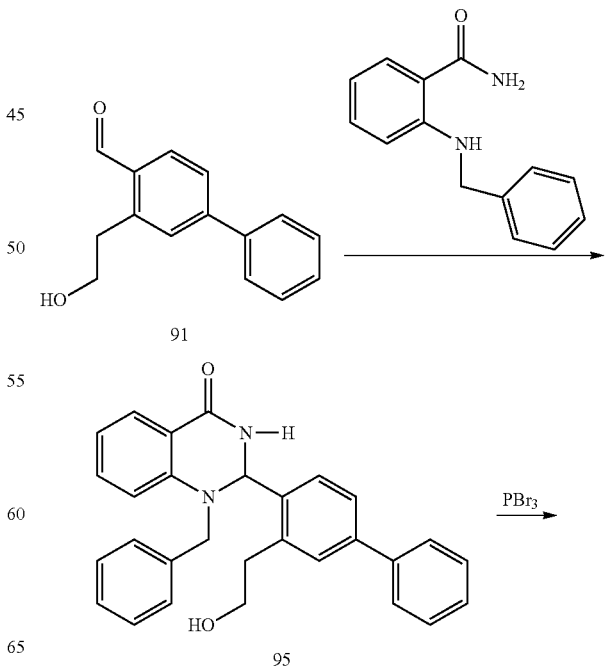

-continued
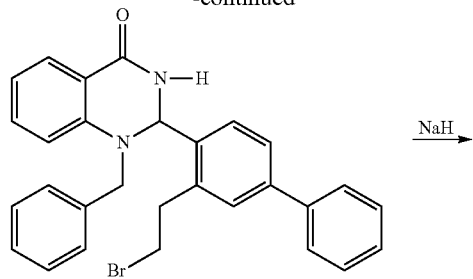
96
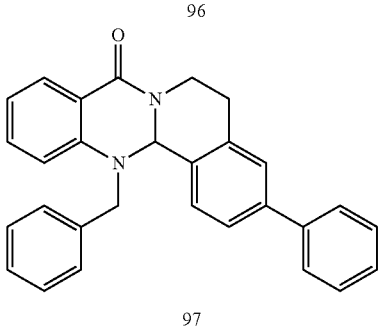
97
NaH →
H₂/Pd →
-continued
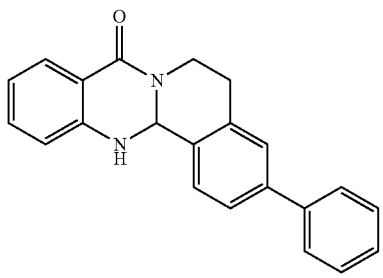
98
The amide attached rigid analogue 91 will be synthesized by condensation of N-benzylanthranilimide with 91 (Scheme 11). Conversion of the alcohol in the bromo derivative 96 and then ring cyclization will afford 97. We will obtain final product 98 by easily deprotecting 97.
Scheme 12. Chiral resolution of SC-2-71.
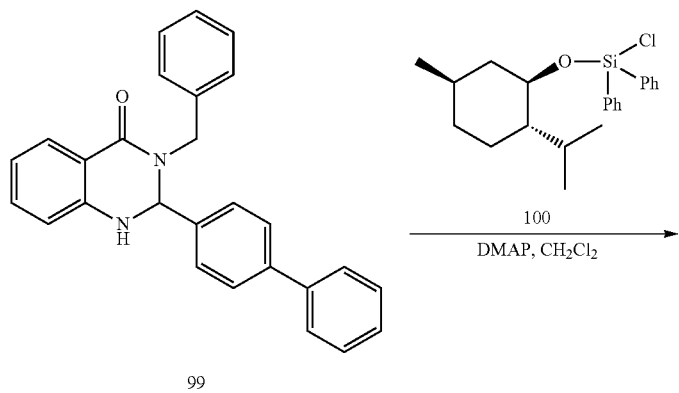
99
100
DMAP, CH₂Cl₂ →
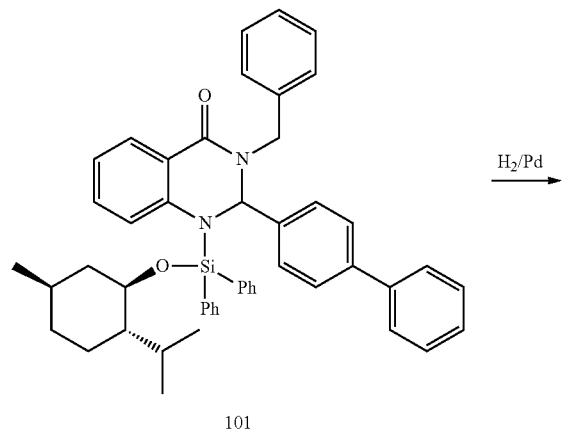
101
H₂/Pd →

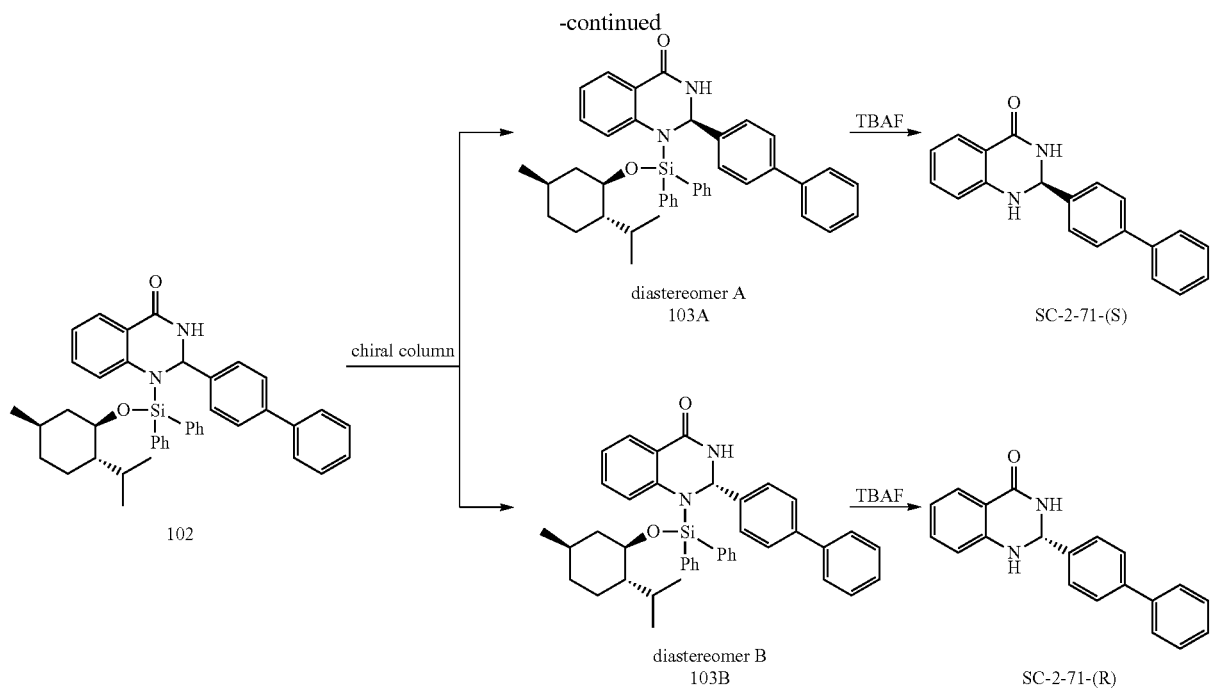

Evaluation of enantioselective actions of SC-2-71 is very important in understanding the molecular interaction with β-tubulin and effects on cell growth. We have designed a straightforward scheme to resolve the enantiomers of SC-2-71 (Scheme 12). Using benzyl protected 99, we will add the chiral siloxane 100 to generate 101. Deprotection of 101 and resolution of 102 on a chiral column will generate two separated diastereomers A and B. The chiral derivatizing agent will be cleaved using TBAF to afford each enantiomer (Scheme 12).

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

What is claimed is:

1. A method of treating cancer in a subject in need thereof, said method comprising administering to said subject a pharmaceutical composition comprising a therapeutically effective amount of at least one compound of having the general structure of formula I,

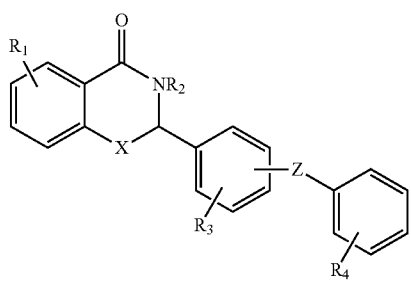

wherein $R_1$, $R_3$, and $R_4$ are independently selected from the group consisting of $NO_2$, H, halo, $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, di- or tri-chloro, and mono-, di- or tri-methyl, $R_2$ is H, or $R_3$ and $R_2$ taken together with the atoms to which they are attached form an optionally substituted heterocyclic fused ring, or $R_3$ and $R_4$ taken together with the atoms to which they are attached form an optionally substituted cycloalkyl fused ring;

X is selected from the group consisting of $NR_5$, and —(NH$(CH_2)_n$)—; wherein n is 1 or 2;

Z is selected from the group consisting of a bond, CO, $C_1$-$C_4$ alkyl, $C_1$-$C_4$ alkenyl, and $C_1$-$C_4$ alkynyl; and $R_5$ is H, or $R_3$ and $R_5$ taken together with the atoms to which they are attached form an optionally substituted heterocyclic fused ring;

thereby treating cancer in a subject; and wherein said cancer is colorectal cancer.

2. A method of treating cancer in a subject in need thereof, said method comprising administering to said subject a pharmaceutical composition comprising a therapeutically effective amount of at least one compound having the general structure,

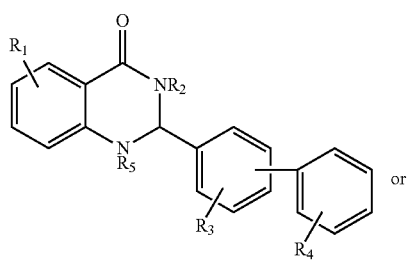

or

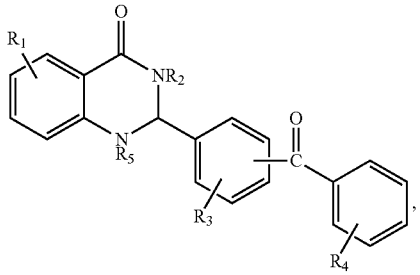

wherein $R_1$, $R_3$ and $R_4$ are independently selected from the group consisting of H, halo and $C_1$-$C_4$ alkyl; and $R_2$ and $R_5$ are H;

thereby treating cancer in a subject; and wherein said cancer is colorectal cancer.

3. The method of claim 2, wherein said subject is a human.

4. The method of claim 1, wherein said subject is a human.

5. The method of claim 1, wherein said at least one compound disrupts β-tubulin polymerization.

6. The method of claim 1, wherein said at least one compound inhibits angiogenesis.

7. The method of claim 1, wherein said at least one compound inhibits a P glycoprotein mediated multi-drug resistant cancer.

8. The method of claim 1, wherein said cancer comprises a mutant p53 protein.

9. The method of claim 1, wherein said pharmaceutical composition is administered via a route selected from the group consisting of topical, oral, buccal, intravenous, intramuscular, intra-arterial, intramedullary, intrathecal, intraventricular, transdermal, subcutaneous, intraperitoneal, intranasal, enteral, sublingual, vaginal, ophthalmic, pulmonary, and rectal.

10. The method of claim 1, wherein said pharmaceutical composition further comprises a therapeutically effective amount of a known chemotherapeutic agent.

11. The method of claim 1, wherein said at least one compound inhibits cancer cell proliferation.

12. The method of claim 1, wherein said at least one compound inhibits endothelial cell proliferation.

13. The method of claim 1, wherein said compound having the general structure of formula I is

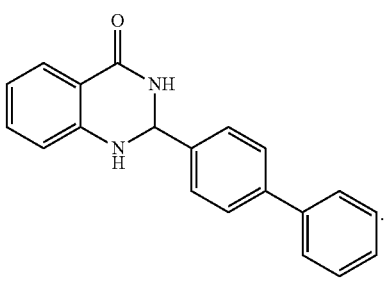
SC-2-71
14. The method of claim 1, wherein said compound having the general structure of formula I is selected from the group consisting of:
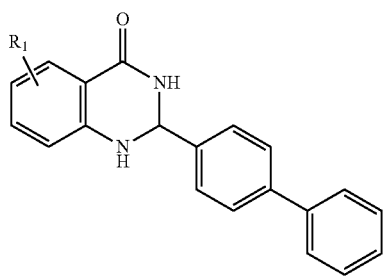
wherein $R_1$ is 2-Cl, 2-CH$_3$, 3-Cl, 3-CH$_3$, 4-Cl or 4-CH$_3$;
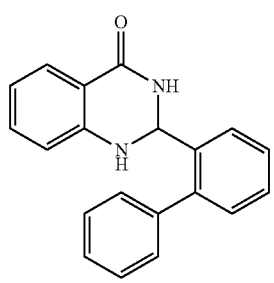
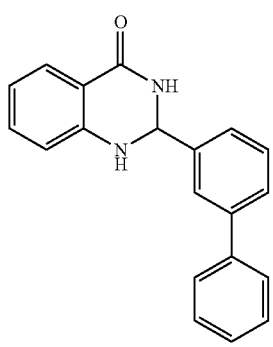
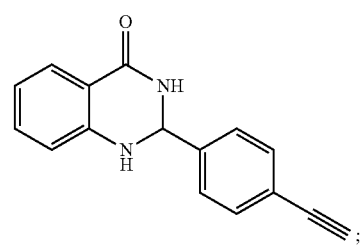
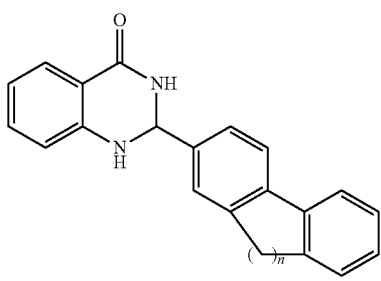
wherein n is 1 or 2;
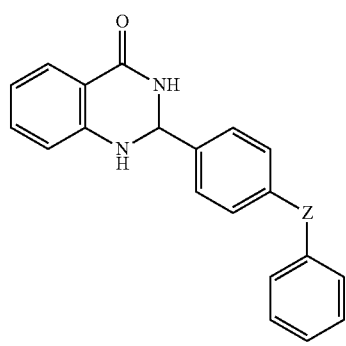
wherein Z is CO, —CH$_2$—, or —C$_2$H$_4$—;
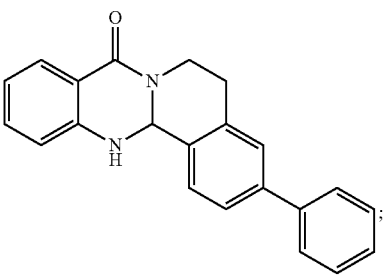
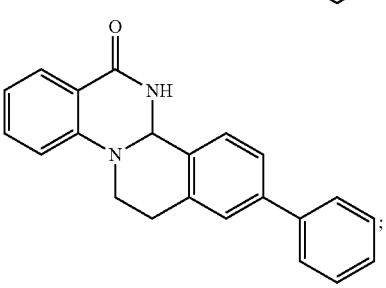
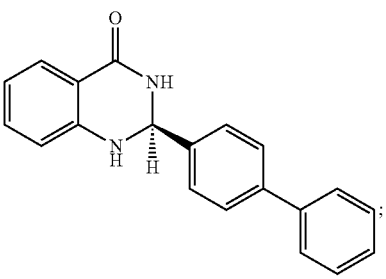

-continued

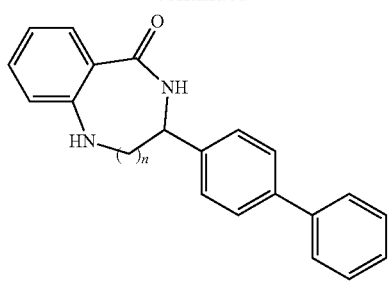

wherein n is 1 or 2;

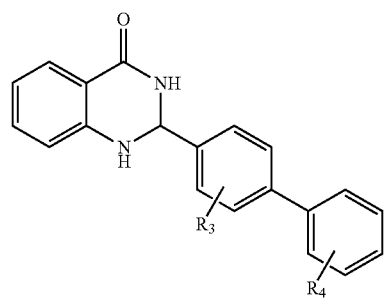

wherein $R_3$ is 2-Cl and $R_4$ is H, $R_3$ is 3-Cl and $R_4$ is H, $R_3$ is 2-CH$_3$ and $R_4$ is H, $R_3$ is 3-CH$_3$ and $R_4$ is H, $R_3$ is H and $R_4$ is 2,3,4-trichloro, or $R_3$ is H and $R_4$ is 2,3,4-trimethyl;

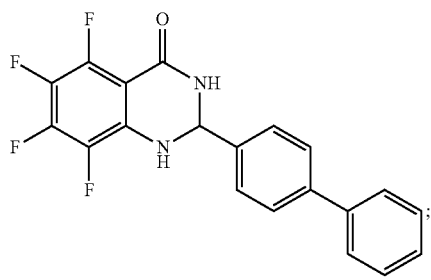

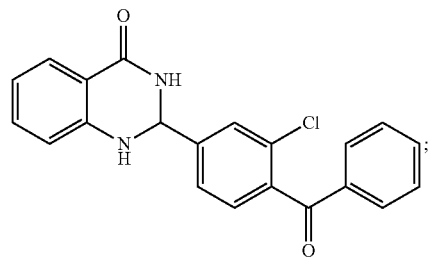

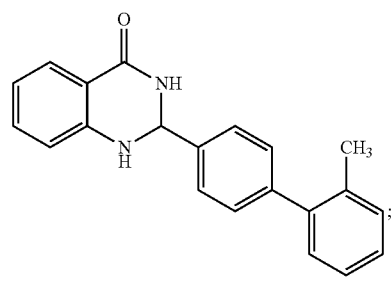

-continued

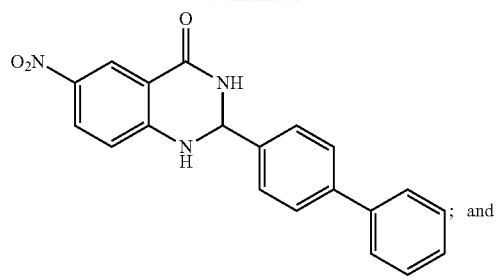

; and

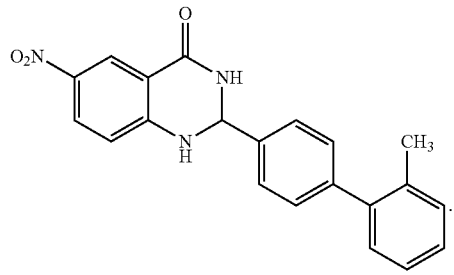

15. The method of claim 1, wherein;

$R_1$, $R_3$ and $R_4$ are independently selected from the group consisting of H, halo, $C_1$-$C_4$ alkyl, $C_2$-$C_4$ alkenyl, $C_2$-$C_4$ alkynyl and $C_5$-$C_6$ aryl;

X is selected from the group consisting of NR$_5$, and —(NH(CH$_2$)$_n$); wherein n is 1 or 2;

Z is selected from the group consisting of a bond, and CO; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

16. The method of claim 1, wherein;

$R_1$, $R_3$ and $R_4$ are independently selected from the group consisting of H, halo and $C_1$-$C_4$ alkyl;

X is NR$_5$;

Z is selected from the group consisting of a bond and CO; and $R_2$ and $R_5$ are H.

17. The method of claim 1, wherein the pharmaceutical composition comprises a pharmaceutically-acceptable carrier and a compound having the general structure of:

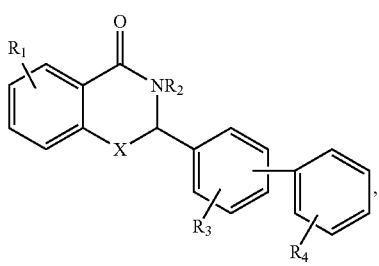

wherein $R_1$, $R_3$ and $R_4$ are independently selected from the group consisting of H, halo and $C_1$-$C_4$ alkyl;

X is NR$_5$; and $R_2$ and $R_5$ are H.

18. The method of claim 1, wherein the pharmaceutical composition comprises a pharmaceutically-acceptable carrier and a compound having the general structure of:

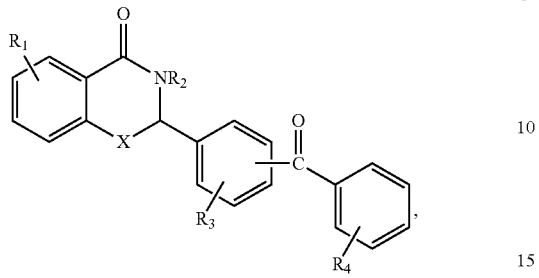

wherein $R_1$, $R_3$ and $R_4$ are independently selected from the group consisting of H, halo and $C_1$-$C_4$ alkyl;
X is $NR_5$; and
$R_2$ and $R_5$ are H.

19. The method of claim 1, wherein the colorectal cancer is an adenocarcinoma.

* * * * *

SEQUENCE LISTING

```
<160> NUMBER OF SEQ ID NOS: 2

<210> SEQ ID NO 1
<211> LENGTH: 449
<212> TYPE: PRT
<213> ORGANISM: Homo sapiens

<400> SEQUENCE: 1

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30
```

```
Ser Gly Asn Tyr Val Gly Asp Ser Asp Leu Gln Leu Glu Arg Ile Ser
         35                  40                  45

Val Tyr Tyr Asn Glu Ala Ser Ser His Lys Tyr Val Pro Arg Ala Ile
 50                      55                  60

Leu Val Asp Leu Glu Pro Gly Thr Met Asp Ser Val Arg Ser Gly Ala
 65                  70                  75                  80

Phe Gly His Leu Phe Arg Pro Asp Asn Phe Ile Phe Gly Gln Ser Gly
             85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Cys Glu Asn Cys Asp
            115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Val Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Ile His Gln Leu
            180                 185                 190

Val Glu Asn Thr Asp Glu Thr Tyr Cys Ile Asp Asn Glu Ala Leu Tyr
            195                 200                 205

Asp Ile Cys Phe Arg Thr Leu Lys Leu Ala Thr Pro Thr Tyr Gly Asp
    210                 215                 220

Leu Asn His Leu Val Ser Ala Thr Met Ser Gly Val Thr Thr Ser Leu
225                 230                 235                 240

Phe Pro Gly Gln Leu Asn Ala Asp Leu Arg Lys Leu Ala Val Asn Met
                245                 250                 255

Val Pro Phe Pro Arg Leu His Phe Phe Met Pro Gly Phe Ala Pro Leu
            260                 265                 270

Thr Arg Arg Gly Ser Gln Gln Tyr Arg Ala Leu Thr Val Pro Glu Leu
            275                 280                 285

Thr Gln Gln Met Phe Asp Ala Lys Asn Met Met Ala Ala Cys Asp Pro
    290                 295                 300

Arg His Gly Arg Tyr Leu Thr Val Ala Thr Val Phe Arg Gly Arg Met
305                 310                 315                 320

Ser Met Lys Glu Val Asp Glu Gln Met Leu Ala Ile Gln Ser Lys Asn
                325                 330                 335

Ser Ser Tyr Phe Val Glu Trp Ile Pro Asn Asn Val Lys Val Ala Val
            340                 345                 350

Cys Asp Ile Pro Pro Arg Gly Leu Lys Met Ser Ser Thr Phe Ile Gly
    355                 360                 365

Asn Ser Thr Ala Ile Gln Glu Leu Phe Lys Arg Ile Ser Glu Gln Phe
370                 375                 380

Thr Ala Met Phe Arg Arg Lys Ala Phe Leu His Trp Tyr Thr Gly Glu
385                 390                 395                 400

Gly Met Asp Glu Met Glu Phe Thr Glu Ala Glu Ser Asn Met Asn Asp
                405                 410                 415

Leu Val Ser Glu Tyr Gln Gln Tyr Gln Asp Ala Thr Ala Glu Glu Glu
            420                 425                 430

Gly Glu Met Tyr Glu Asp Asp Glu Glu Glu Ser Glu Ala Gln Gly Pro
            435                 440                 445

Lys
```

<210> SEQ ID NO 2
<211> LENGTH: 427
<212> TYPE: PRT
<213> ORGANISM: Bos taurus

<400> SEQUENCE: 2

```
Met Arg Glu Ile Asp His Ile Gln Ala Gly Gln Cys Gly Asn Gln Ile
  1               5                  10                  15

Gly Ala Lys Phe Trp Glu Val Ile Ser Asp Glu His Gly Ile Asp Pro
                 20                  25                  30

Thr Gly Ser Tyr His Gly Asp Ser Asp Leu Gln Leu Glu Arg Ile Asn
             35                  40                  45

Val Tyr Tyr Asn Glu Ala Ala Gly Asn Lys Tyr Val Pro Arg Ala Ile
 50                  55                  60

Leu Val Asp Leu Glu Pro Gly Thr Met Asp Ser Val Arg Ser Gly Pro
 65                  70                  75                  80

Phe Gly Gln Ile Phe Arg Pro Asp Asn Phe Val Phe Gly Gln Ser Gly
                 85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ser Glu Ser Cys Asp
            115                 120                 125

Cys Leu Gln Gly Phe Gln Leu Thr His Ser Leu Gly Gly Gly Thr Gly
130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
            195                 200                 205

Asp Ile Cys Phe Arg Thr Leu Lys Leu Thr Thr Pro Thr Tyr Gly Asp
210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
            275                 280                 285

Leu Thr Gln Gln Met Phe Asp Ala Lys Asn Met Met Ala Ala Cys Asp
290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ser Ala Thr Phe Ile
            355                 360                 365

Gly Asn Ser Thr Ala Ile Gln Glu Leu Phe Lys Arg Ile Ser Glu Gln
370                 375                 380
```

```
Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp
                420                 425
```